(12) United States Patent
Monroe

(10) Patent No.: US 8,044,778 B2
(45) Date of Patent: Oct. 25, 2011

(54) INJECTION DEVICE AND CASE WITH REPORTING ABILITY

(75) Inventor: O. Napoleon Monroe, Huntington, NY (US)

(73) Assignee: Henry Schein, Inc., Melville, NY (US)

( * ) Notice: Subject to any disclaimer, the term of this patent is extended or adjusted under 35 U.S.C. 154(b) by 328 days.

(21) Appl. No.: 12/319,792

(22) Filed: Jan. 12, 2009

(65) Prior Publication Data

US 2009/0128330 A1    May 21, 2009

Related U.S. Application Data

(63) Continuation-in-part of application No. PCT/US2007/015922, filed on Jul. 12, 2007.

(60) Provisional application No. 61/198,794, filed on Nov. 10, 2008.

(51) Int. Cl.
*B60R 25/10* (2006.01)
*G08B 13/14* (2006.01)
*G05B 19/00* (2006.01)

(52) U.S. Cl. ........... 340/426.19; 340/539.13; 340/572.1; 340/10.1; 340/5.1; 340/5.8; 340/426.22

(58) Field of Classification Search ................. None
See application file for complete search history.

(56) References Cited

U.S. PATENT DOCUMENTS

| 2004/0100379 A1* | 5/2004 | Boman et al. ............ 340/539.26 |
| 2004/0233041 A1* | 11/2004 | Bohman et al. ............... 340/10.1 |
| 2005/0252259 A1* | 11/2005 | Ekstrom ......................... 70/257 |
| 2006/0192652 A1* | 8/2006 | Mandava et al. ................ 340/5.8 |
| 2007/0005953 A1* | 1/2007 | Boman et al. .................. 713/100 |
| 2007/0273484 A1* | 11/2007 | Cederlof et al. ........... 340/10.33 |
| 2008/0143523 A1* | 6/2008 | Ekstrom .................... 340/545.6 |
| 2009/0194104 A1 | 8/2009 | Van Sickle |
| 2009/0251295 A1* | 10/2009 | Norair et al. ............... 340/10.51 |
| 2010/0232320 A1* | 9/2010 | Twitchell, Jr. ................ 370/254 |
| 2010/0253519 A1* | 10/2010 | Brackmann et al. ....... 340/572.1 |
| 2010/0265068 A1* | 10/2010 | Brackmann et al. ....... 340/572.1 |

* cited by examiner

*Primary Examiner* — Julie Lieu
(74) *Attorney, Agent, or Firm* — Brenda Pomerance

(57) ABSTRACT

A container for a product uses a location circuit for determining the location of the container, a storage element for storing a container identification code, a plurality of data acquisition components for acquiring status of at least two characteristics of at least one of the container, the product and a user of the product, and a communication interface for generating and sending a communication signal including (a) the container identification code from the storage element, (b) the location of the container from the location circuit, and (c) the status of the at least two characteristics from the data acquisition components. The container may be an auto-injector for containing a medicament, or a case for containing an item such as an auto-injector. Generally, the location circuit uses the global positioning system (GPS). The data acquisition components are chosen from a camera, and at least one sensor for sensing at least one of a thermal image, vibration, temperature, humidity, a chemical and an audio signal. The characteristic may be use of the product, or lack of use of at least one of the container and the product.

96 Claims, 15 Drawing Sheets

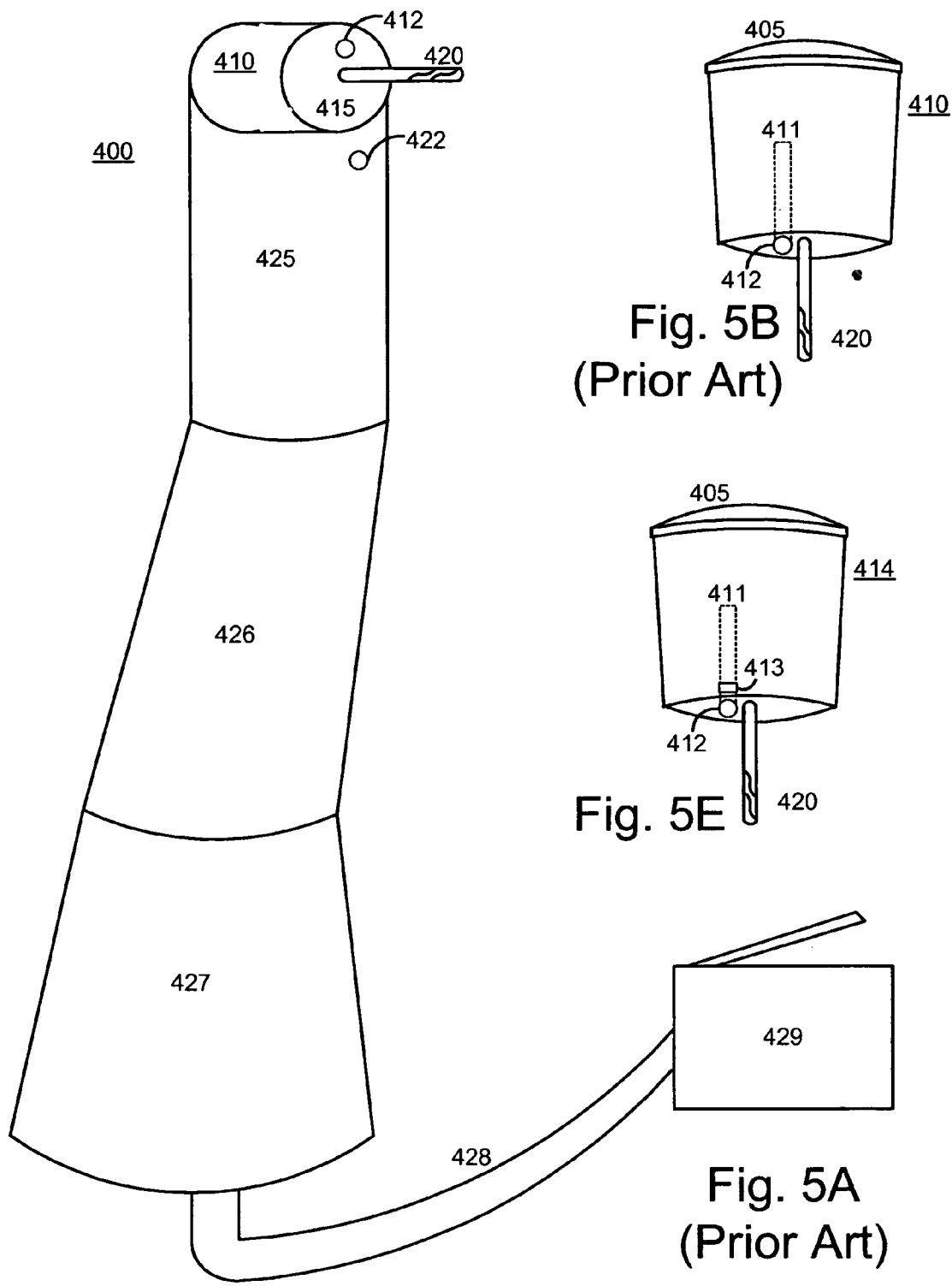

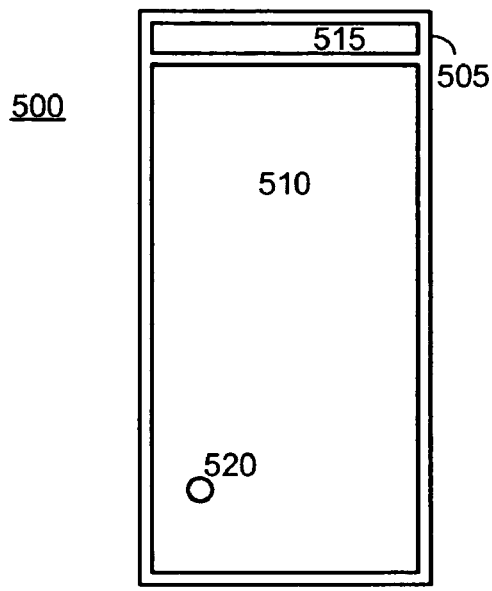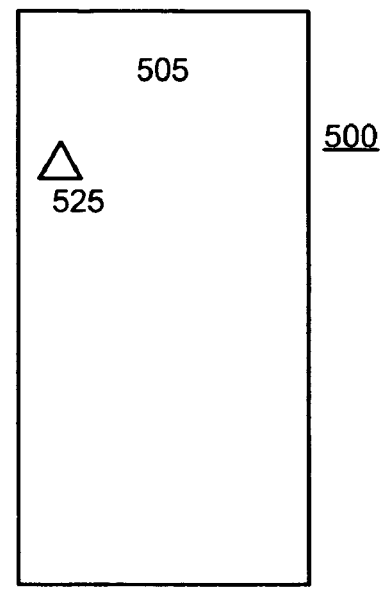
Fig. 9A
(Prior Art)
Fig. 9B
(Prior Art)
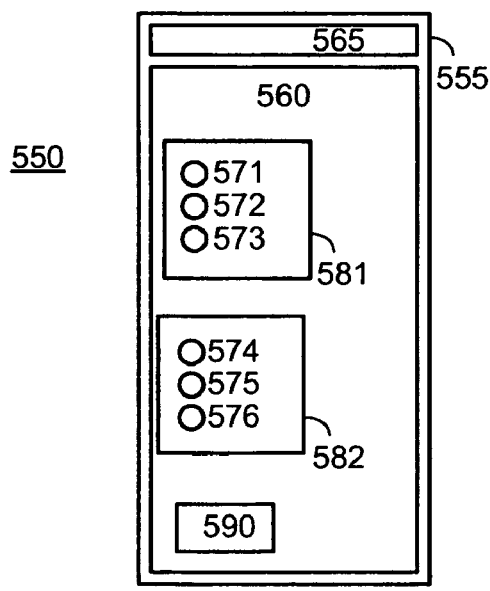
Fig. 10

INJECTION DEVICE AND CASE WITH REPORTING ABILITY

This application claims priority from U.S. patent application Ser. No. 61/198,794, filed Nov. 10, 2008. This application also claims priority from PCT patent application Ser. No. PCT/U.S. Ser. No. 07/15922, filed Jul. 12, 2007, which in turn claims priority from U.S. patent application Ser. Nos. 11/485,820, 11/485,828 and 11/485,829, each filed on Jul. 13, 2006, and having a common inventor and assignee herewith.

BACKGROUND OF THE INVENTION

The present invention relates to a case for injecting medicament, and more particularly, is directed to a case having data collection and reporting ability that reports events to a central facility.

For medical products, such as pharmaceuticals and devices, some government regulations define information about the product as being part of the product. Regulations from different governments may conflict.

Certain government regulations further define the "label" for a medical product as comprising certain information affixed to the product's container as well as certain information accompanying the product, such as a written sheet with usage instructions or other information.

Government regulations for medical products differ by country, and may include requirements such as:
 making information available in Braille or audio for blind or partially-sighted customers,
 providing usage instructions in particular language(s),
 recording and reporting, within a first time period, of fatal or life-threatening experiences with the medical product,
 recording and reporting, within a second time period, of serious, unexpected, adverse experiences with the medical product,
 recording and reporting, within a third time period, of all adverse experiences with the medical product,
 storing, for a fourth time period, of all correspondence relating to experiences with the medical product, and
 ability to track a medical product through its life-cycle, defined as all or part of manufacturing, distribution and usage.

Further, a single medical product may be subject to different regulatory or procedural regimes, depending on how the product is used, e.g., given by a physician, or used by a consumer at home.

Best practices suggest that recording negative quality experiences, adverse reactions and other information associated with lot numbers or serial numbers helps focus quality initiatives.

In regions such as Europe, a medical products manufacturer or distributor may have to comply with preparing product labels in approximately 20 different languages.

A product distributor is a party other than the manufacturer, end user, or end user's medical services provider. Thus, a pharmacy can serve as a distributor.

Internet Publication http://www.devicelink.com/pmpn/archive/98/09/005.html discloses a medical packaging system for a medical products manufacturer, which utilizes a multilingual labeling sub-system in order to comply with European multiple-language labeling requirements. The sub-system scans a route sheet for a specific product code, and then compiles variable text, including language(s) for labels. A medical products manufacturer uses a language database, programs its printers to pull information from the database, and prints on packages produced from form-fill-seal machines.

It will be appreciated that the needs and capabilities of a manufacturer are different than those of a distributor. For branded products from certain manufacturers that are distributed by multiple distributors, being able to prove that problem products were distributed by other than a specified distributor is of interest. Specifically, in products liability lawsuits where it is substantially impossible to prove which distributor distributed the problem products, it may be the case that liability is assigned to all distributors typically in proportion to their market share. Thus, the distributors with the largest market share have an interest in proving that the problem products came from distributors other than themselves.

U.S. Publication No. 20030229543 to Shannon M. Zimmerman et al. relates to centralized management of packaging data with rule-based content validation, which provides an online environment whereby manufacturers manage packaging data for their products. FIG. 14 illustrates translations data entry window 108E of user interface 101 that allows the user to select one or more languages 136 for translation and printing on a label of the packaging data. In this manner, any text printed on the label may be multilingual. Another concern for medical products is that the device be properly programmed and used. For example, infusion pumps should be programmed to dispense the correct dose. At present, each device has its own user interface and terminology including dosing units. Further, nurses calibrate devices in different ways: manually, via monitors, or via the device itself. Some hospitals develop rule libraries of drug dosing units and dosage limits, and they load the rule libraries into the devices, along with actions required and/or suggested if something is out of range. It has been proposed to add monitoring and interruption capability to patient-controlled infusion devices.

Some medical devices are too small to have barcode labels affixed to the device. Affixing such labels particularly increases labeling, storage and transportation costs. Some small manufacturers are unwilling to invest in labeling systems to comply with lot and expiration barcode requirements, or affixing radio frequency identification (RFID) tags.

It is known to print information such as a bar code with electrically conductive ink. As used herein and in the claims, bar code refers to a conventional bar code, a data matrix, and techniques for representing printed information in condensed form relative to alphanumeric text.

Mobile communications have been proposed in the health area. SIMpill, a South African firm, makes a small device that clips on to a medication bottle and sends a text message to a central computer when the cap is removed. If no message arrives, the central computer sends a text message reminder to the patient's mobile phone.

As another example, LG, a South Korean handset manufacturer, sells a phone with a built-in blood glucose meter, for use by diabetics, that transmits readings to a computer for further analysis.

A further example is the AlleCare P3 holster for an Epipen, described at www.allecare.com. An Epipen is an injector containing Epinephrine that delays anaphylactic reaction to allergy, the anaphylactic reaction possibly leading to death. The P3 holster transmits a satellite location signal when the Epipen is removed therefrom. If the signal is not deactivated within a minute, an operator notifies emergency services that the user is in crisis.

Another example is U.S. Pat. No. 6,992,580, assigned to Motorola, Inc., that discloses a portable communication device with two sensors, for sensing the user's environment and/or a biometric characteristic of the user, such as heart rate. An example, from the automotive field, of transmitting sensor readings in conjunction with location is the General Motors OnStar system. Within seconds of a moderate to severe vehicle crash, the vehicle's OnStar module will send a message to the OnStar Call Center (OCC) through a cellular connection, informing an advisor at the call center that a crash has occurred. A voice connection between the advisor and the vehicle occupants is established. The advisor then can conference in 911 dispatch or a public safety answering point (PSAP), which determines if emergency services are necessary. If there is no response from the occupants, the advisor can provide the emergency dispatcher with the crash information from the vehicle's sensing and diagnostic module that reveals the severity of the crash. The dispatcher can identify what emergency services may be appropriate. Using the Global Positioning System (GPS) satellites, OnStar advisors are able to tell emergency workers the location of the vehicle.

As another example, it is known to place a GPS sensor on a portable x-ray machine.

It is expected that government regulations, the needs of customers for more information, as well as the desire to provide more features to customers, will result in increasing demands relating to the scope and availability of product information. For example, when customers can track their goods through the distribution process, the customers can treat distributor facilities as the customers' inventory warehouses.

Accordingly, there is room for improved communication regarding the status of emergency devices.

SUMMARY OF THE INVENTION

In accordance with an aspect of this invention, there is provided a container for a product, having a location circuit for determining the location of the container, a storage element for storing a container identification code, a plurality of data acquisition components for acquiring status of at least two characteristics of at least one of the container, the product and a user of the product, and a communication interface for generating and sending an emergency communication signal including (a) the container identification code from the storage element, (b) the location of the container from the location circuit, and (c) the status of the at least two characteristics from the data acquisition components.

The container may be an auto-injector for containing a medicament, or a case for containing an item such as an auto-injector. Generally, wherein the location circuit uses the global positioning system (GPS). The data acquisition components are chosen from a camera, and at least one sensor for sensing at least one of a thermal image, vibration, temperature, humidity, a chemical and an audio signal. The characteristic may be use of the product, or lack of use of at least one of the container and the product.

In accordance with another aspect of this invention, there is provided a container for a product, the container for use with an external device having long-range communication capability and short-range communication capability and location sensing capability, comprising a storage element for storing an access code for a central facility and a container identification code, a plurality of data acquisition components for acquiring status of at least two characteristics of at least one of the container, the product and a user of the product, a local communication interface for communicating with the external device using the short-range communication capability of the external device, and a processor for producing information and directing the local communication interface to send the information to the external device. The information produced by the processor and sent to the external device includes (a) the access code for the central facility, (b) the container identification code, (c) the status of at least two characteristics from the data acquisition components, (d) instructions for the external device to use its location sensing capability to sense its location and to report its sensed location to the central facility along with (b) and (c), using its long-range communication capability and (a).

It is not intended that the invention be summarized here in its entirety. Rather, further features, aspects and advantages of the invention are set forth in or are apparent from the following description and drawings.

BRIEF DESCRIPTION OF THE DRAWINGS

FIGS. 5A-5D are views of a conventional dental handpiece;

FIG. 5E is a view of a handpiece with a problem indicator;

FIGS. 9A-9B are views of a conventional sterilization pouch;

FIG. 10 is a view of an embodiment of a sterilization pouch;

DETAILED DESCRIPTION

Figure 1:
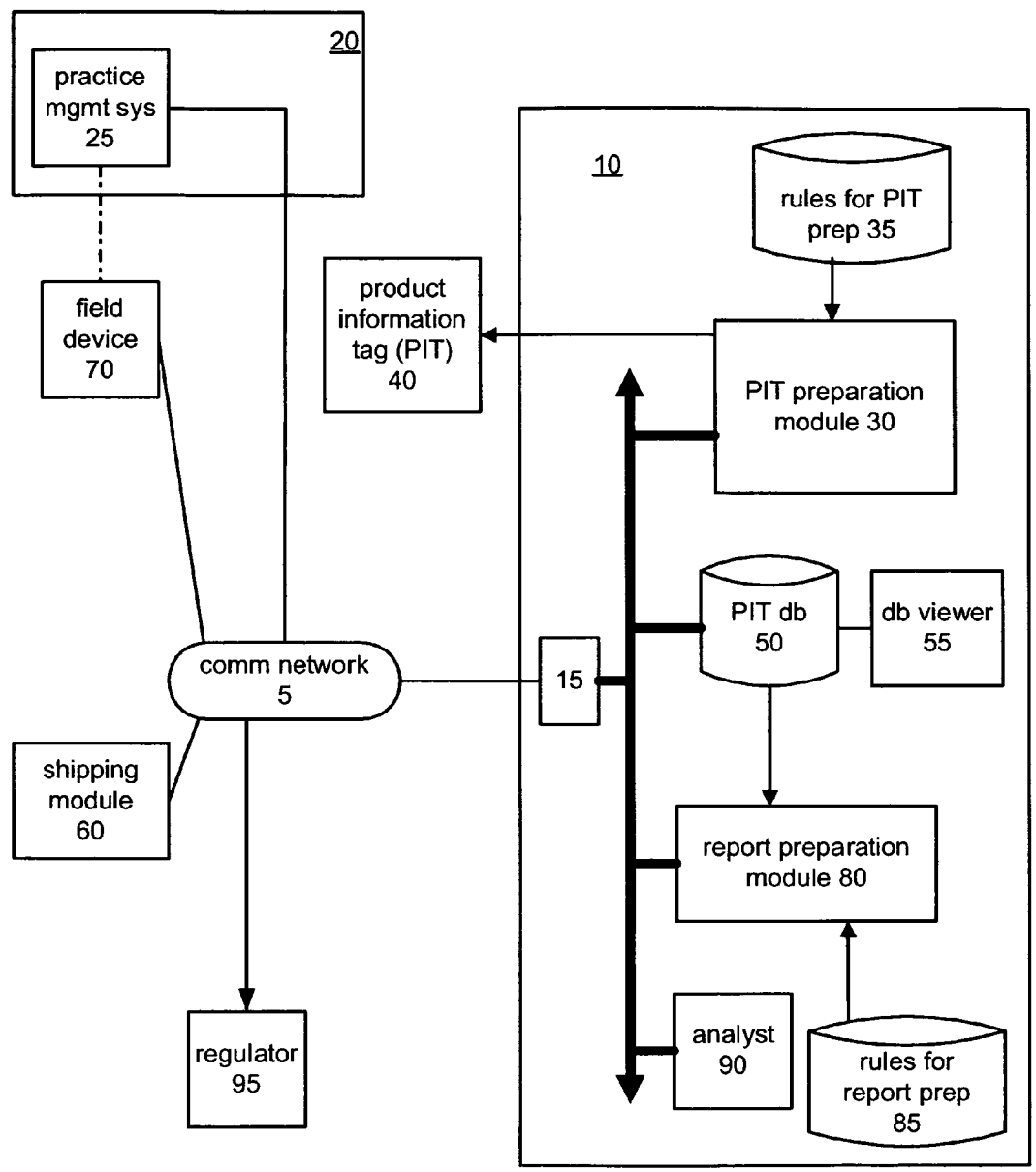
FIG. 1 is a block diagram showing product management system 10.

Referring now to the drawings, and in particular to FIG. 1, there are illustrated communication network 5, product management system 10, customer 20, customer practice management system 25, shipping module 60, field device 70 and regulator 95.

Communication network 5 may be any wireline or wireless network, such as the Internet, a private virtual network, a private dedicated network and so on. Further, communication network 5 may be embodied as a plurality of networks, for example, a wireline data network and a wireless voice network.

Product management system 10 includes communications interface 15, product information tag (PIT) preparation module 30, PIT preparation rules 35, PIT database 50, database viewer 55, report preparation module 80, report preparation rules 85, and analyst 90.

Product management system 10 is embodied as a general-purpose computer programmed in accordance with the present description. The general-purpose computer can be one computer or many computers networked together. System 10 can operate on dedicated or shared hardware, and may be at a user's premises or available as a so-called "web service" through communication network 5 or other communication facility. When system 10 is available as a web service, analyst 90 communicates therewith via communication network 5, in similar manner as regulator 95.

Customer 20 is able to communicate with product management system 10 via communication network 5. In some embodiments, customer 20 has a general purpose computing device, such as a personal computer. In other embodiments, customer 20 has practice management system 25 which may be any conventional system for storing medical or dental patient records, modified to also store PIT and other information described below, for example, the DENTRIX® system available from Henry Schein, Inc. A typical practice management system has a front-office portion for handling appointment scheduling and payments, a mid-office portion for handling patient records and a back-office portion for handling diagnostic and treatment information, as well as a patient portal enabling a patient to access their appointments and medical information via a communication network such as the Internet. In the examples described below, it is contemplated that information associated with products by a products distributor is captured by practice management system 25 and associated with the appropriate patient record.

In some embodiments, practice management system 25 uses communication network 5 to provide information to product management system 10, such as product usage and location information, and/or to receive information from product management system 10, such as recommended operating instructions and product supply chain information.

PIT preparation module 30 is adapted to generate PITs for products in accordance with customer order 20 and PIT preparation rules 35. Products typically are medical or pharmaceutical supplies, such as drugs or devices.

As used herein and in the claims, "PIT" means a record relating to a product that logically accompanies the product, and that may or may not physically accompany the product in whole or in part. In contrast, a "label", as the term is customarily used in the medical products industry, must physically accompany the product and include required standardized information.

A PIT may be embodied in any of the following ways: (a) as a printed paper affixed to a product or a product's container, (b) as a printed paper accompanying a product, (c) as an electromagnetic device affixed to or accompanying a product that stores information, (d) as an electromagnetic device affixed to or accompanying a product that enables access to information stored about the product, the information being stored in other than the electronic device that serves as the PIT, (e) combinations of the above, or (f) other configurations apparent to one of ordinary skill. Thus, a PIT may be information associated with a paper, such as a bar code, and/or information associated with an electronic or magnetic device.

Electronic devices suitable for a PIT include a radio frequency identification (RFID) tag, a "smart card" typically comprising a credit-card sized device with a processor and memory, a pattern that is magnetically readable as a bar code, and other devices that will be apparent to those of ordinary skill in the art.

Generally, the PIT serves to uniquely identify the product relative to other products in PIT database 50.

Customer 20 provides an order that typically includes identification of the desired product, quantity, a ship-to address, an order date and sometimes a delivery date and/or other special instructions. The instructions may be provided directly or indirectly. An example of indirect instructions is when a customer is in a country whose regulations stipulate certain requirements; the customer is deemed to have indirectly provided the certain requirements. The customer order may specify features of the product, for example, the type of container, and optional features such as stickers for patient charts, the stickers bearing product-related information, and characteristics of the patient that affect the packaging, such as disabilities (need for Braille stickers), childproof containers and so on.

PIT preparation rules 35 include product handling information based on the type of product, e.g., refrigerated, customer predefined preferences, shipping company requirements, regulatory requirements in the country of origin, regulatory requirements in the destination country, destination country characteristics such as official language(s), customs requirements, climate characteristics of the shipping path and destination (e.g., cold or hot packs needed), and special instructions in or related to the customer order.

The information in PIT preparation rules 35 relates to:

package layout and appearance;

what type of PIT or PITs should be used, i.e., sticker on product, sticker on patient's chart, product insert, electronic tag, bar code, device to be attached to patient, reorder stickers or devices;

what historical information about the product content must be on its PIT: lot code, manufacturer date, serial number, UPC code and so on;

patient-specific requests and/or requirements, such as Braille labels, audible label devices, childproof containers, easy-open containers, and so on;

PIT information for the product container: whether refrigerated shipping is needed, individual container, package container, carton container, shipping pallet and so on;

when the product is a refill, how to reset or relabel the refilled container;

associated products, e.g., syringes for fluids;

product trademark requirements;

proper representation of trademarks and associated designs in translations (e.g., font, accompanying designs, different trademarks in different countries);

promotional materials;

advice to include restrictions to be applied (ex: how to use, how to distribute, how to store);

whether a sensor is to be applied, and what type sensor may be appropriate;

training materials;

training schedules;

maintenance and repair instructions;

maintenance and repair schedules;

programming rules for the PIT, such as which phone number or Internet protocol (IP) address to contact when triggered (see discussion below of injector 600 and case 700), or when training is required for an associated healthcare professional, patient or caregiver (that is, individuals for some items should be periodically or as-needed trained or retrained on use of the item);

information related to communicating post-shipment information, such as if a product complaint has to be forwarded within a predetermined number of days after the complaint is received, if the complaint should generate a warning message or a reminder to appropriate parties such as the manufacturer;

repair reminders after a certain number of uses and or elapsed time since last repair; and sending compliance and/or training reminders to patients, medical providers and so on, as directed by manufacturers, regulations, doctors or as requested by patients.

For example, let it be assumed that the customer order specifies that 100 units of high speed dental operatory handpieces are to be sent to a location in Moldova and are to have RFID tags with serial numbers. PIT preparation rules 35 specify that Moldova requires medical device instructions to be in Russian and in French, that the manufacturer of such handpiece as identified under Moldovian regulations be determinable, although not necessarily from the product PIT; that the customer wants its instruction sheets to have its name on the sheets and other monitoring information, and the instructions in German and English, and its name affixed to the product itself; and that the regulatory requirements for Korea, the country of manufacture, specify that the date of manufacture must be on the PIT for the device.

In this example, PIT preparation module 30 creates PITs having stickers to be affixed to the handpieces having the customer name and the date of manufacture, creates inserts on paper having instructions for use in Russian, French, German and English, and creates RFID tags and sterilization indicators to be affixed to the handpieces containing the serial number of the respective handpieces.

When PIT preparation module 30 generates PIT 40, it also generates a PIT record and places the PIT record in PIT database 50. The PIT record includes at least the information provided in the PIT, and typically includes additional information. The PIT record serves as an audit trail for the past, present and future information about the product. Generally, the past information refers to the manufacturing history of the product, including manufacturer, product type, product serial number and UPC code, product version number, manufacture date, expiration date (if any), previous owners of the product, whether the product has been subject to recalls and field corrective actions, the number of previous sterilization procedures, vibration, shock, radiation, temperature and/or humidity extremes in storage conditions, and so on. The present information refers to instructions for use, which can be in one or more languages, or contain one or more pointers to instructional language, the present location of the product, and so on. The future information refers to the customer, the product's actual use, the shipper, the shipment route (if appropriate) and so on.

The customer may be a health care professional, such as a product prescriber or dispenser and/or a patient (product user) and/or a patient's caregiver.

Supply chain information refers to information relating to how a product arrived at its current location, particularly, who had possession of the product, when, and the conditions experienced by the product while in a party's possession, such as ambient temperature and humidity ranges. A location sensing system, such as the global positioning system (GPS), can be a source of supply chain information. Information relating to where and when a product was can be correlated with third-party information such as transit route information and/or weather service data, to determine cumulative time that a product was outside a temperature range, ambient conditions at the time of use, and so on.

In some embodiments, the PIT record includes information provided to the customer, as well as information provided from the customer, or the product itself while in the customer's possession.

During the lifetime of the product, the definition of present and future adapts. That is, after the product is received by the customer, the shipper becomes part of the past information. Usage and exception reports are then provided by the customer and/or the product, as discussed below.

Database viewer 55 enables a person, such as analyst 90, to view the contents of PIT database 50. Database viewer 55 is embodied as software for interacting with PIT database 50. Analyst 90 represents and suitable hardware for enabling a person to view information, such as a terminal or personal computer and/or printer. Database viewer 55 typically enables analyst 90 to formulate queries and apply them to PIT database 50. Many commercial database packages are known and suitable, such as Microsoft Access, MySQL, Oracle and so on.

PIT database 50 may be used for the following purposes:
to provide information to manufacturers for sales programs and recalls,
to provide information for product liability lawsuits quantifying the amount of product from a particular products distributor involved in malfunctions and the like,
for data mining,
to project product failure rates and the need to replace the product and/or maintain an inventory of spare replacement parts,
to indicate which customers to focus on based on the customer's activity with regard to various procedures,
to recommend complementary or substitute products,
to provide different levels of customer support depending on the value of the customer,
to update training, maintenance or repair instructions or schedules,
to help decide where to locate sales and/or service centers, typically near the most frequent users of products.

Shipping module 60 enables the shipping service to update the PIT record, to indicate the present location of the product. Package tracking services are well known, and employed by, for example, UPS, Federal Express and the United States Post Office. In some embodiments, shipping module 60 is part of system 10, and queries the shipper's package tracking service for the status of products in transit. Shipping module enables a person or system associated with a shipping service to update the PIT record. Additionally, if a shipper has field device 70, PIT 40 may update the PIT record.

Field device 70 enables a customer or other authorized party to access a PIT record, and to update a PIT record with usage and exception information. Each PIT record may contain not only actual product usage information, but also supply chain information for the product. In some embodiments, field device 70 also transmits PIT and possibly other information directly to practice management system 25, so that the PIT and other information can be associated with patient records, enabling a patient record to directly provide product supply chain information. FIGS. 2A-2F show embodiments of field device 70.

Field device 70 can be located at any point along the product supply chain, including shipper premises, doctor premises and patient premises.

Usage information refers to customary activity that the product is involved in. For example, if the product is a device or medicine, the fact that it was subjected to temperatures above a first threshold or below a second threshold at any time is a usage event. If the product is a medicine, the fact that it was used (ingested, applied, etc.) by a patient on a certain date and time is a usage event. Lack of usage is also a form of usage information. Another example of a usage event is being dropped.

Exception information relates to an abnormal event associated with the product. For example, if the product is a device, a device failure is an exception event. If the product is a medicine, a side-effect in the patient, such as an allergic reaction, is an exception event.

In a simple case, the customer submits a usage and/or exception event via a written or faxed letter, possibly using a form.

Figure 2A:
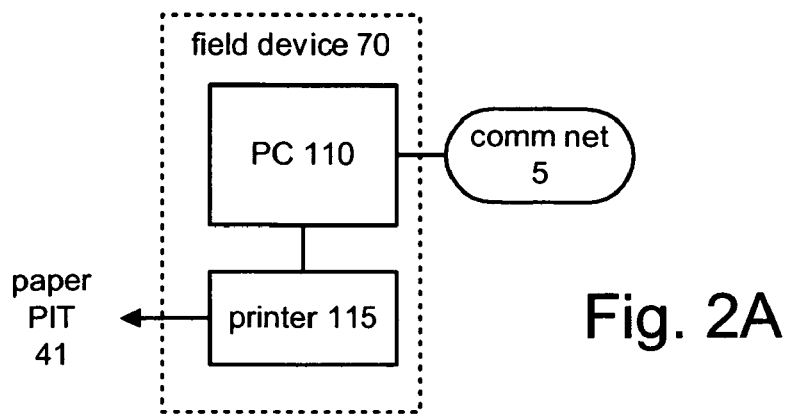
FIGS. 2A-2F are block diagrams showing embodiments of field device 70.

FIG. 2A shows field device 70 as comprising customer personal computer (PC) 110 and printer 115. Here, the customer communicates with PIT database 50 via electronic mail, or via a website. In some cases, the product PIT may need to be updated, and the updating occurs using printer 115. It will be appreciated that PC 110 may be a desktop, laptop, tablet or handheld personal computer, or a personal digital assistant, or even a cellular telephone with suitable processing ability.

Field device 70 is shown coupled to communication network 5. It will be understood that this coupling represents a path to a central computer, such as product management system 10, and/or, in some embodiments, to a local computer such as practice management system 25.

Figure 2B:
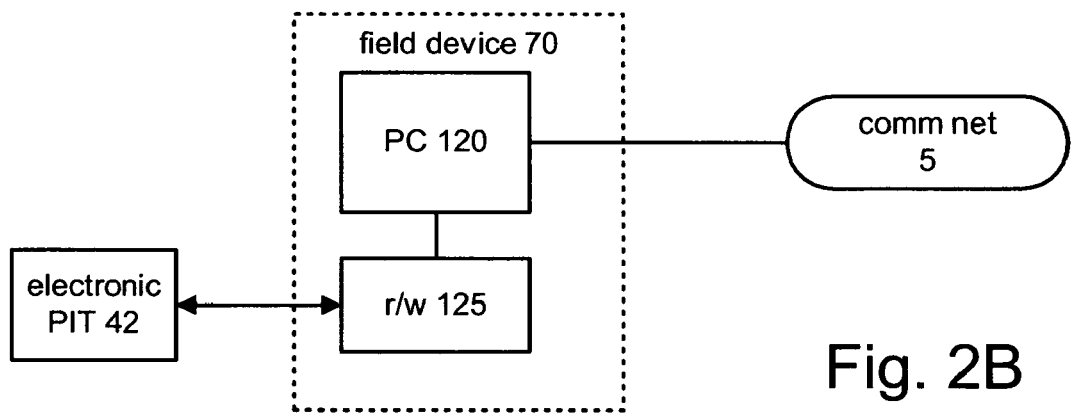

FIG. 2B shows field device 70 as comprising customer PC 120 and reader/writer 125. Here, the product bears or is associated with electronic PIT 42, such as an RFID tag or smart card. Reader/writer 125 reads information from electronic PIT 42, and passes the read information to PC 120, which in turn uses the read information to access the desired PIT record from PIT database 50. When PC 120 updates the PIT record, PIT database 50, or a program running in PC 120, may update electronic PIT 42 accordingly.

Figure 2C:
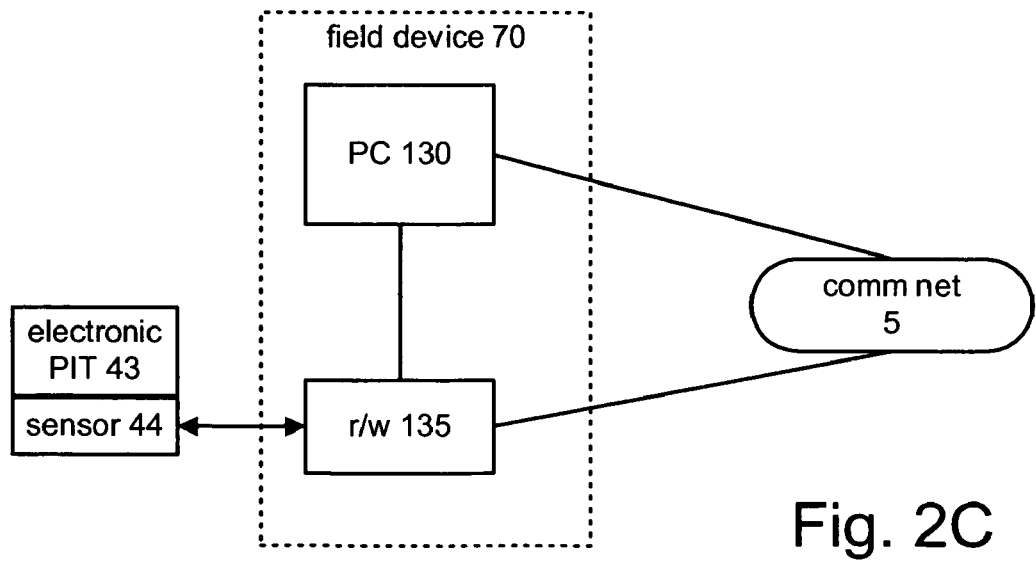

FIG. 2C shows field device 70 as comprising PC 130 and reader/writer 135. PC 130 and reader/writer 125 can communicate with each other, and each can communicate directly with PIT database 50. Here, the product bears or is associated with electronic PIT 43 and sensor(s) 44. Sensor 44 is adapted to detect regular usage events and some exception events, and to provide this information to electronic PIT 43. In some embodiments, sensor 44 also provides detected usage events and exception events directly to PIT database 50, for example, via wireless communication or via daily "synchronization" sessions or via as-needed synchronization sessions. In a synchronization session, the product communicates with PIT database 50, generally to provide information to PIT database 50. PC 130 is able to query PIT database 50, and also to report usage and/or exception events that are beyond the capability of sensor 44.

For example, if the product is a dental handpiece for holding drill bits, also referred to as burrs, sensor 44 may detect temperatures over a high threshold, such as 220° F., indicating that the handpiece has been subjected to a sterilization procedure; and also may detect temperatures under a low threshold, such as 40° F., indicating that the handpiece has been subjected to a lubrication procedure. That is, handpiece lubrication is often performed using a spray having a propellant that creates low temperatures.

As another example, high value implants such as heart pacemakers, titanium posts screwed into bones, dental implants, artificial knees and the like may have an embedded sensor that can be wirelessly read, in combination with a product information tag, to provide device status.

Figure 2D:
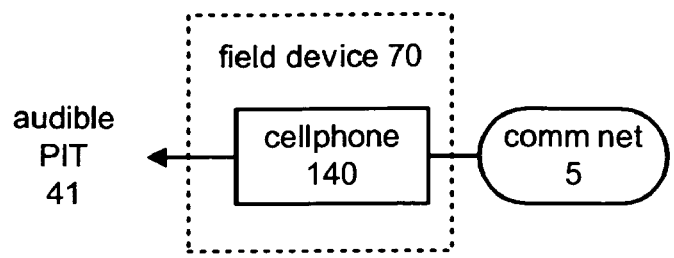

FIG. 2D shows field device 70 as comprising cellphone 140. Here, the customer uses cellphone 140 to call system 10 and verbally inquire about the PIT record and/or verbally provide a usage and/or exception event. Security measures may be employed, such as ensuring that the calling customer is actually the customer to whom the product was shipped.

Cellphone 140 may have a camera and/or location sensing ability, such as GPS capability. When this is the situation, cellphone 140's features may be used in data collection and reporting, such as usage or exception events.

Figure 2E:
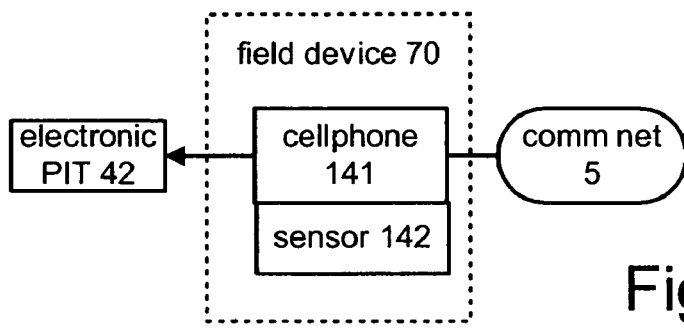

FIG. 2E shows field device 70 comprising cellphone 141 and sensor 142 that automatically places a call to provide sensed information. In other embodiments (not shown) field device 70 comprises a multi-media device, able to send and receive video and audio information, and also data, and possibly able to print data. When field device 70 is a multi-media device, the PIT information may comprise multi-media. For example, the usage instructions may be a video with closed-caption text and audio, explaining how to use the medical product. This form of presentation is particularly helpful for handicapped and/or illiterate people.

Field device 70 may be a programmable infusion pump for providing a drug. Typically, an infusion pump is programmed to provide a quantity of drug based on the bodyweight of the patient, sometimes with the ability for a patient to manually request more drug up to a predetermined maximum amount. The usage pattern of this device, combining its programming and the patient's manual requests, can be captured as part of a clinical trial, to correlate usage to outcome.

Similarly, for a dental restoration (filling), the usage of a combination of devices, e.g., a composite resin or other restorative material and at least one of a desterilizer, bonding agent, dental drill, laser apparatus and etchant, can be correlated with the clinical record and the patient outcome, to identify best usage techniques. In general, when a combination of medical devices and/or drugs are used together, it is helpful to know of the concurrent usage.

Figure 2F:
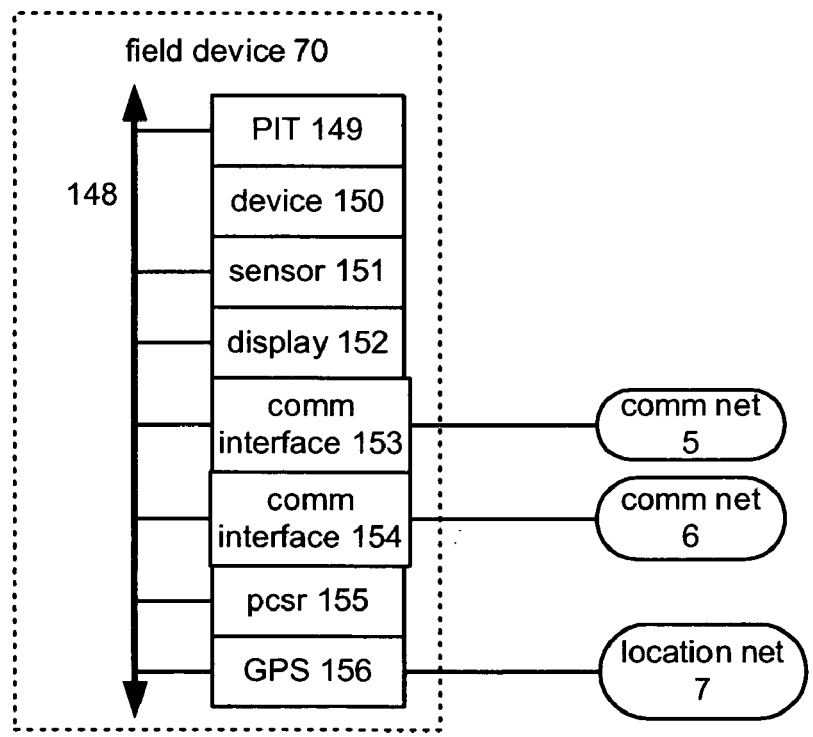

FIG. 2F shows field device 70 comprising internal communication network 148, PIT 149, device 150, sensor 151, display 152, remote interface 153, local interface 154, processor with memory 155, and location assembly 156. Internal communication network 148 may be a bus or a plurality of point-to-point connections. Sensor 151 senses at least one operating condition of device 150. In one instance, device 150 is a dental handpiece, and sensor 151 is a bimetallic sensor that disengages one or more burr-moving elements of the handpiece when a predetermined temperature is reached, to prevent overheating, as shown in more detail in FIG. 8A below. Audiovisual display 152 displays an indication of the operating condition of device 150 to its user, such as a dentist. When sensor 151 is triggered into sensing an event, either by usage of device 150 or by a poll received from remote interface 153 or local interface 154, sensor 151 activates location assembly 156 to communicate with location network 7, such as the global positioning system, to obtain the location of device 150 as a location stamp. Processor with memory 155 stores readings from sensor 151 in association with a time stamp and the location stamp, and provides the stored sensor readings and associated time stamp and location stamp to one or both of remote interface 153 and local interface 154, for transmission to product management system 10 and practice management system 25, via remote communication network 5 and local communication network 6, respectively.

The device of FIG. 11 is an embodiment of the configuration of FIG. 2F.

In some embodiments, a biometric reader, such as a fingerprint reader, voice recognizer, retinal scanner or the like, is used to determine who is using device 150, and/or the identity of the patient receiving services via device 150. In other embodiments, a barcode scanner is used to input the identity of the user and/or patient. The identity information is typically associated with the PIT information in practice management system 25, but may be anonymized or absent from product management system 10 due to privacy concerns.

In some embodiments, interfaces 153, 154 and processor with memory 155 are in a cradle that device 150 having sensor 151 is placed into.

In combination with the PIT information, the sensor readings are analyzed to assess the cause for unexpected failure of a device or class of devices. Analysis occurs as product management system 10, practice management system 25, field device 70, or combinations thereof. A cause of failure may include usage patterns. Such assessment could be the basis for notifying the operator of a potential problem, offering maintenance training to operators predicting future product failures, and avoiding product liability.

One of the concerns of dentists in using certain light cured materials, such as material used to fill a tooth cavity, is the degree of cure accomplished during curing. To measure the amount of curing, a sensor is supplied with or built into the formulation of such light cured material.

An example of a sensor supplied with the material is a membrane radiometer placed proximal to the material, between the material on and/or in the tooth and the light source that measures the amount of light reaching the material, estimates therefrom the amount of curing and indicates when the estimated amount of curing (or amount of light) has reached a predetermined threshold. Another example of a sensor supplied with the material is an external transducer for measuring the hardness of the cured material.

An example of a sensor built into the light cured material is a material that changes color when a certain temperature is reached. Another example of a built-in sensor is a tiny transducer that measures pressure change, indicating the hardness of the cured material.

In some cases, multiple sensors are simultaneously operative. For example, device 150 may be a pouch that an instrument is placed into, and then the pouch is placed in a sterilization device, such as an autoclave, an oven or other device, to raise the contents of the pouch to a sterilization temperature. Here, the pouch has a sensor, the instrument has a sensor, and the sterilization device has a sensor. One example of a pouch sensor is an ink that changes color based on its temperature. Another example of a pouch sensor is a so-called integrator ink that changes color based on the amount of time it has been at or above a temperature threshold and a predefined relative humidity. Pouch sensors can include chemical, optical, electronic, mechanical, or electromechanical devices, and so on.

Figure 3:
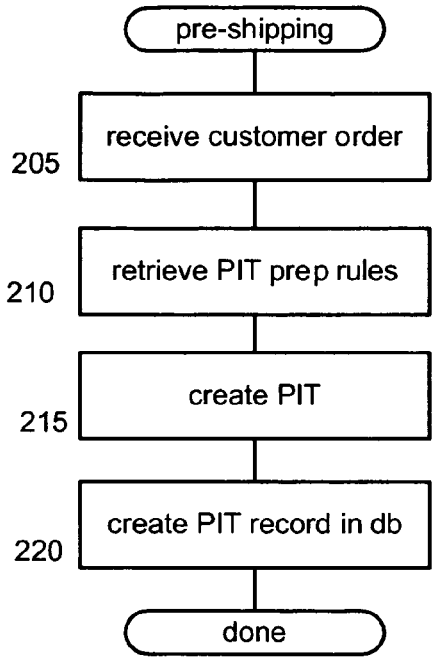
FIG. 3 is a flowchart showing pre-shipment processing.

FIG. 3 is a flowchart showing pre-shipment processing.

At step 205, a customer order is received. At step 210, PIT preparation module 30 retrieves PIT preparation rules from PIT preparation rules 35. At step 215, module 30 creates PITs in accordance with the customer order and PIT preparation rules. At step 220, module 30 creates a PIT record in PIT database 50.

Figure 4:
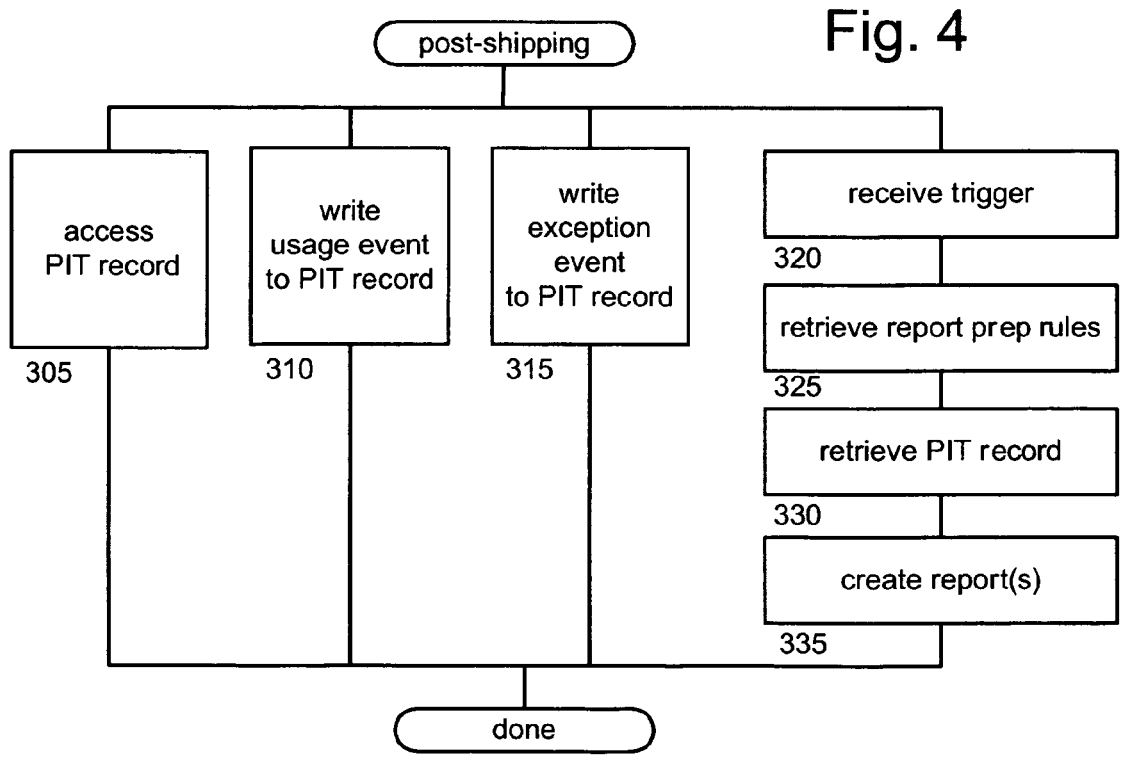
FIG. 4 is a flowchart showing post-shipment processing.

FIG. 4 is a flowchart showing post-shipment processing.

In one scenario, at step 305, a PIT record is accessed, via database viewer 55 or field device 70. The requested record is provided, and processing is complete.

In another scenario, at step 310, a usage event is written to a PIT record. The usage event may be provided via field device 70, or manual input (not shown) corresponding to the situations where the usage event is provided via telephone, fax or paper mail.

In another scenario, at step 315, an exception event is written to a PIT record. The exception event may be provided via field device 70, or manual input (not shown) corresponding to the situations where the exception event is provided via telephone, fax or paper mail.

In another scenario, at step 320, a trigger is received, such as a periodic trigger corresponding to time of day/week/month, or a one-time trigger corresponding to receipt of an exception event. At step 325, report preparation module 80 retrieves report preparation rules from report preparation rules 85. At step 330, module 80 retrieves one or more PIT records. At step 335, module 80 creates report(s) 90 in accordance with the PIT records and report preparation rules 85.

Report(s) 90 comprise:

regulatory reports, such as reports of exception events, particularly adverse patient reactions, that may be electronically delivered to regulator 95, customer activity reports that are directed to how much and/or how often a product is being used, typically delivered to analyst 90, repair reports in the form of reminders, return shipping documents or the like, training response reports indicating satisfactory completion of training, customer satisfaction reports that indicate problems and customer comments both good and bad, typically delivered to analyst 90, and re-order reports that are automatically generated as a product is used up or reaches the end of its lifetime and are electronically delivered to customer 20.

Report(s) 90 are based on data collected from and/or in association with PIT 40 while the product associated with PIT 40 is possessed by the product distribution, and other parties having possession of the product subsequent to the product distributor, including the shipper, the medical services provider such as doctor or dentist, and perhaps the ultimate patient.

To a distributor, an important piece of information is the customer's probable need or desire to reorder. Some distributors sell or supply scanners to customers, the scanners are for reading barcode labels identifying the products, so that reordering is accomplished via scanning. Typically, the barcode is unique to each manufacturer and carries the manufacturer's part number. Some distributors also affix their own bar code labels to a product, so that the product has two bar code labels, one from the manufacturer and the other from the distributor. In some cases, the customer, such as a large hospital chain or a dental school, may also affix its own bar code label to the product, so that the product has three bar code labels. Since the various bar code labels use different formats, depending on the source of the label, it is helpful to have an automated translation table between the various bar codes, to ensure, inter alia, that a product is properly recognized.

With suitable access authorization, analyst 90 can update PIT preparation rules 35 and report preparation rules 85.

A handpiece is a unit, typically used in the medical and dental professions, that is held in the hand of the party providing services to the target. The handpiece has a rapidly rotating member for altering the target, such as a patient's tooth. Each handpiece has a power source; there are three types of power sources: air turbine, electric motor and air motor. An air turbine is used in a high speed turbine handpiece. An electric motor or air motor is used with a gear drive handpiece attachment, such as a contra-angle attachment.

An air turbine has a rotor located in the head of the handpiece. An air turbine handpiece's rotor is usually supported on each side by a bearings. When there is a problem, such as dirt build-up, the turbine typically stops working altogether. Prior to ceasing operation, the heat caused by the handpiece may burn a patient. Its repair cost is fairly small. Typically, the turbine is repaired about 6-12 times during the 7-10 year life of the handpiece.

For each of the electric motor and the air motor, the motor itself is attached to the gear drive handpiece attachment at its distal end, away from the burr and thus away from the patient. A drive shaft connects to the gear drive handpiece in both air and electric driven motors. The gear drive handpiece has a series of gears and bearings to deliver reduced, unaltered or accelerated rotational speed, or a combination of speeds with other movements, depending on the type of procedure to be performed. The final gears, where the cutting burrs are attached, are supported by multiple bearings. When there is a problem, such as damage to a part of the gear drive, dirt build-up or partial or significant bearing failure, an electric or air motor continues to apply drive that creates excess friction that in turn creates excess heat, and the gear drive handpiece can become so hot that the patient is burned. An electric or air motor by its nature applies more torque for cutting. The repair cost of a gear drive handpiece can be up to ten times the repair cost of an air turbine rotor. An advantage of using a micromotor (an air motor or electric motor) is that with the correct ratio, such as 1 to 5 increasing speed gear ratio of a gear drive handpiece, it is possible to reach controlled sustained speeds, such as 200 krpm, at the cutting burr with 5-6 times more torque than is possible with a high speed turbine handpiece, which in turn provides greater control of the cutting power, decreased cutting time and better dentistry.

FIGS. 5A-5B show conventional dental handpiece 400 having head 410, stem 425, handle 426, base 427, tube 428 and foot pedal 429. Head 410 is generally in the shape of a cylinder having face 415 and push button 405 opposite face 415. Burr 420 is a removable drill bit inserted into the center of face 415. Burr 420 can be fluted metal or unfluted diamond particles fused to a stainless steel shaft. Push button 405 is used to release burr 420 from handpiece 400. Head 410 includes internal light guide 411 terminating at light cap 412 in face 415, which serves as a light for illuminating what is being drilled by burr 420.

Handpiece 400 can be a high speed turbine handpiece or a gear drive handpiece. A high speed turbine handpiece generally has stem 425, handle 426 and base 427 formed as one unit. A gear drive handpiece generally has stem 425 and handle 426 formed as one unit, while base 427 is a separate unit having a motor.

In some cases, instead of light emanating from head 410, stem 425 has an internal light guide terminating at light cap 422, located so that light emanating from light cap 422 illuminates what is being drilled.

In operation, a dentist actuates foot pedal 429, causing power to be supplied via tube 428 to a high speed turbine handpiece, or to an air or electric driven micro-motor attached to a gear drive handpiece, that causes burr 420 to rotate. In some cases, tube 428 also supplies power to a light source, e.g., a bulb or light emitting diode (LED), that generates light transmitted through light guides inside handpiece 400. Each of a high speed turbine handpiece and a gear drive handpiece has bearings inside its head.

Figure 5C:
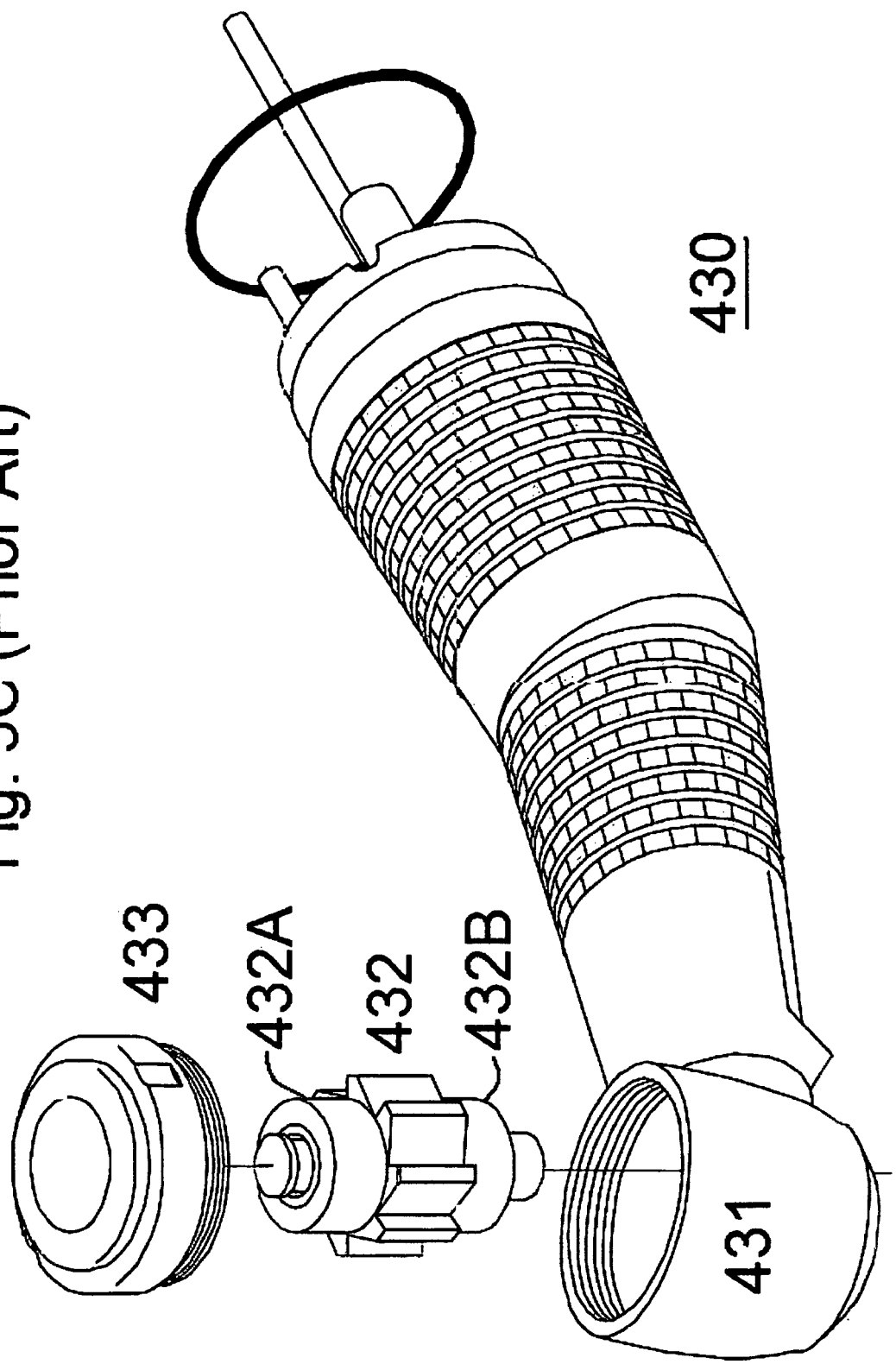

FIG. 5C shows high speed turbine handpiece 430 with a turbine rotor, having head casing 431, turbine rotor 432 with bearings 432A, 432B attached on each side thereof, and back cap 433. Rotor 432 is air-driven, with speeds reaching 400,000 rpm. Air is driven into the bottom of handpiece 430, shown on the right side in the drawing. It is possible for head casing 431 or back cap 433, that is in close proximity to the revolving rotor, to become heated by a failure or degradation event such as the failure of the bearings, dirt, wear or mechanical damage such as dropping the handpiece, use of an eccentric burr, or a partial depression of the back cap by a dentist.

Figure 5D:
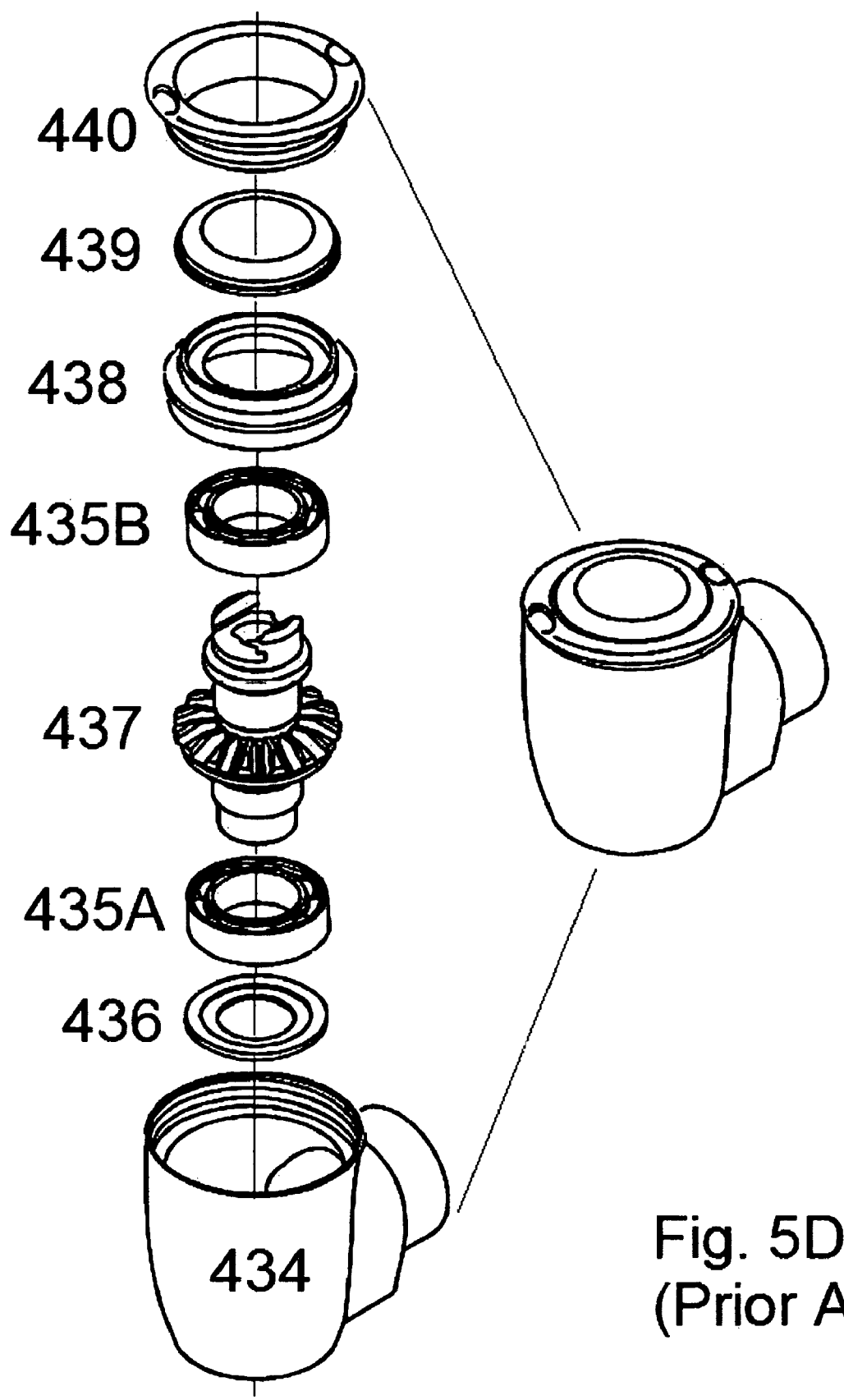

FIG. 5D is an exploded view of the head gear assembly of a gear drive handpiece. Head cover 434 contains bearings 435A, 435B, washer 436, final gear drive 437, spacer 438, membrane 439 and back ring 440. When assembled, membrane 439 and back ring 440 form a back cap. One of the causes of failure or degradation, generally referred together as failure, of a handpiece is normal wear and tear. Other causes of failure of a handpiece are poor maintenance, poor cleaning, inappropriate repair and/or dropping or mis-use. In some cases, poor maintenance manifests itself by a change in the operating characteristics of the product. An example of this would be the build up of heat in handpieces which have not been properly cleaned and lubricated internally. With the movement of dental practitioners toward an electric rather than an air-powered handpiece, this maintenance becomes even more important. With an electric or air powered handpiece, the electric drive motor will continue to move the gears even though there is a build-up of foreign material within the handpiece. The foreign material will cause friction and result in heat build-up. It has been reported that this has caused temperatures to rise to the extent that patients have been injured.

Measuring the heat of the handpiece, and/or its vibration and/or its speed, is useful for detecting whether a handpiece is performing properly. Speed can be measured indirectly through vibration or noise frequency. Vibration can indicate rotational speed too high for a given procedure.

FIG. 5E shows handpiece head 414 of either a high speed turbine handpiece or a gear drive handpiece. Handpiece head 414 is similar to handpiece head 410, described above, except that handpiece head 414 includes problem indicator 100413, such as a filter or lens between light guide 411 and light cap 412. In operation, when a problem such as failure or degradation occurs, problem indicator 100413 interferes with the light from light guide 411, such as by changing the color of the light or blocking the light entirely, to alert the dentist or other handpiece user that a problem exists.

Figure 6A:
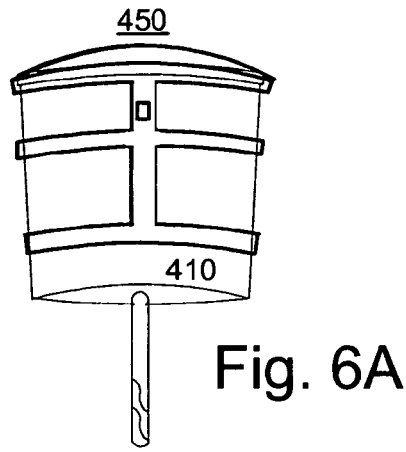
FIGS. 6A-6B are views of one embodiment of a clip-on girdle for a handpiece.
Figure 6B:
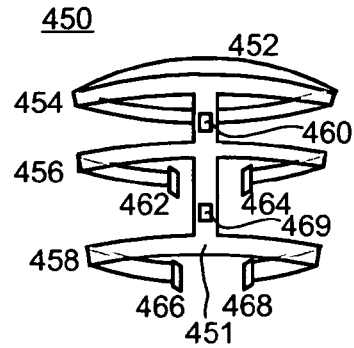

FIGS. 6A-6B are views of girdle 450 intended to clip on to handpiece 400, specifically, to wrap around handpiece head 410. Girdle 450 has spine 451, back support 454 having flexible membrane 452, back detection band 456 and front detection band 458. Detection band 456 has vibration sensor 462 at one end, and temperature sensor 464 at its other end. Detection band 458 has vibration sensor 466 at one end, and temperature sensor 468 at its other end. Sensors 462, 464, 466, 468 are generally in respective planes orthogonal to the planes of the ends of detection bands 458, 456; in some embodiments, the sensors are in the same plane as the detection bands. Spine 451 has product information tag 460 and sterilization sensor 469.

Girdle 450 may be formed of any suitable substance or combination of substances, such as a lightweight flexible metal for detection bands 456, 458, bimetallic material for sensors 464, 468 and piezoelectric material for vibration sensors 462, 466. Sterilization sensor 469 may be ink that changes color in response to temperature. Temperature sensors 464, 468 can change shape in response to temperature, as is typical for a bimetallic material, and/or can change color. Vibration sensors 462, 466 can change color in response to vibration.

Operation of girdle 450 will now be discussed.

Handpiece 400 is typically sterilized after each use. Similarly, girdle 450 is sterilized after each use, such as by putting girdle 450 in an autoclave (steam sterilizer) or other device designed to sterilize, such as an electron beam sterilizer, a gamma radiation sterilizer, or submersion in a liquid sterilant or an ethylene oxide sterilizer. In some cases, sterilization raises the ambient temperature so that the temperature on the surface of girdle 450 reaches a predetermined temperature, or the ambient temperature reaches a predetermined temperature. Sterilization sensor 469, which may be printed ink that changes color when the predetermined conditions have been reached, serves to verify that sterilization of girdle 450 has occurred. Sterilization sensor 469 may be reset by applying pressure thereto, or via another suitable reset method.

After sterilization, girdle 450 is placed on head 410 so that flexible membrane 452 covers push button 405, back detection band 456 is generally over the back bearing, and front detection band 458 is generally over the front bearing.

Flexible membrane 452 enables the dentist to remove burr 420 from handpiece 400 by pressing push button 405. Flexible membrane 452 may advantageously block some force applied to push button 405, such as when a dentist improperly rests push button 405 against a surface, or uses handpiece 400 as a patient cheek retractor.

When handpiece 400 reaches a temperature above its normal operating temperature, the normal operating temperature being defined relative to each type of handpiece, the back of head 410 typically is hottest, and this temperature is picked up by back support 454 and communicated to detection bands 456, 458 via spine 451.

Detection band 456, being flexible, is responsive to the vibration and temperature caused by the back bearing. When the vibration of detection band 456 exceeds a first vibration threshold, vibration sensor 462 triggers, such as by changing shape or color. When the temperature of detection band 456 exceeds a first temperature threshold, temperature sensor 464 triggers, such as by changing shape or color. The triggering of a sensor indicates to the dentist that maintenance is needed.

Handpiece vibration can be caused by a chipped, worn, damaged or eccentric burr, by faulty construction, by build-up of dirt, or by another cause.

Detection band 458 operates in similar manner as detection band 456, except that band 458 is responsive to the front bearing.

In some embodiments, the sensor triggering is communicated to product information tag 460 and/or a processor or controller, such as in FIG. 2C, via wireline or wireless communication. Depending on the legal regulations of the country and design factors, the processor may then cut off power to the handpiece, or otherwise disengage burr-moving elements, to ensure that the handpiece is not permitted to operate while it is too hot, thereby preventing harm to the patient.

Figure 7A:
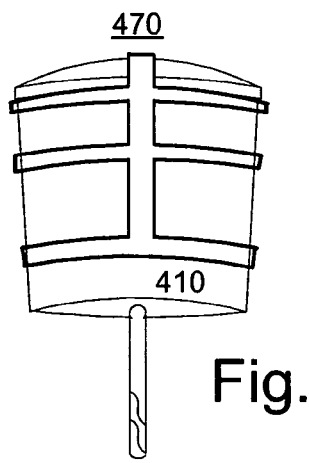
FIGS. 7A-7B are views of another embodiment of a clip-on girdle for a handpiece.
Figure 7B:
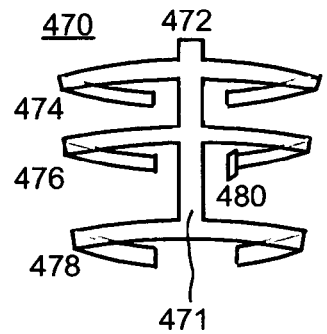

FIGS. 7A-7B are views of girdle 470, which is similar to girdle 450 except that girdle 470 has stabilizer clip 472 at its rear, instead of a flexible membrane, and has only one sensor.

Figure 8A:
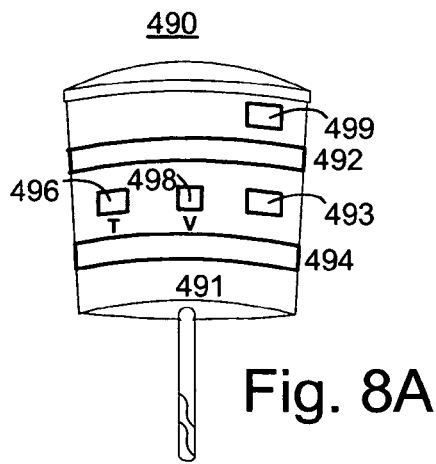
FIGS. 8A-8B are views of a handpiece according to the present invention.
Figure 8B:
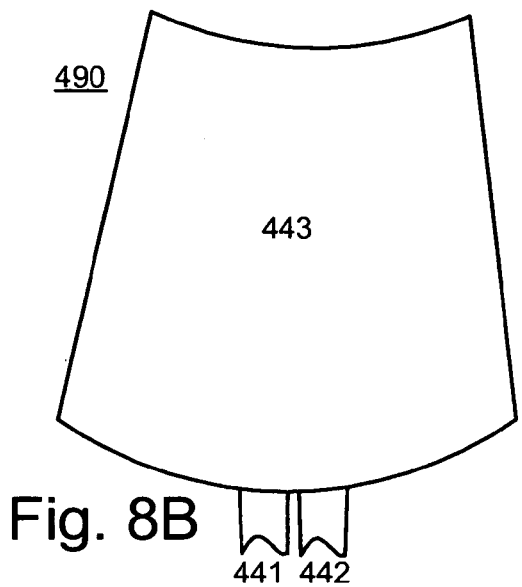

FIGS. 8A-8B are views of handpiece 490, which is generally similar to handpiece 400. For brevity, only the differences will now be discussed.

Handpiece 490 has head 491 having built-in detection bands 492, 494, product information tag 493, temperature indicator 100496, vibration indicator 100498, and sterilization indicator 100499. Detection bands 492, 494 may be on the outside of head 491, the inside of head 491, or located in cut-out areas of head 491, as shown. Similar to detection bands 456, 458, detection bands 492, 494 respectively serve to detect temperature and vibration from the back and front bearings of handpiece 490. Respective temperature and vibration sensors, similar to those described above with respect to girdle 450, are located inside head 491, and cause indicators 100496, 498 to light when appropriate thresholds are passed. Sterilization sensor 499 is similar to sterilization sensor 469 of girdle 450.

Handpiece 490 has base 443 having cords or pipes 441, 442 extending therefrom to a controller (not shown in FIGS. 8A-8B, but generally shown in FIG. 2C). Cords or pipes 441, 442 represent a flexible shaft and/or an air delivery mechanism and/or a electrical power connection and/or an electrical connection for communication, depending on the type of handpiece. Cord 441 provides power, similar to cord 428 of handpiece 400. Pipe 442 provides electrical signals from the temperature and vibration sensors of head 491, and possibly signals to and from PIT 493, as generally shown in FIG. 2C. The controller is able to terminate power to the handpiece when the operating characteristics of the handpiece are deemed to be unacceptable.

In some embodiments, the sensors in handpiece 490 terminate power to the handpiece when the appropriate thresholds are passed.

In some embodiments, the user of handpiece 490 is given the opportunity—but is not required—to indicate to the controller that usage instructions were read prior to use. The controller stores the indication, if provided, which is useful for subsequent investigations if a problem arises with the handpiece. In other embodiments, the controller requires that the user of handpiece 490 certify that usage instructions were read before enabling power to handpiece 490.

FIGS. 9A-9B are views of conventional sterilization pouch 500 having back 505, front 510 and adhesive strip 515. Typically, back 505 is formed of paper while front 510 is formed of transparent plastic. Front 510 is permanently affixed to back 505 along three edges. The unaffixed edge of front 510 is opposite adhesive strip 515. When the portion of back 505 bearing adhesive strip 515 is folded over the unaffixed edge of front 510, the unaffixed edge becomes affixed and a pouch is formed. Imprinted on the side of back 505 facing the pouch is temperature sensor 520, formed of thermally sensitive ink, which changes color when a predetermined temperature is reached. On the side of back 505 outside the pouch is sensor 525, formed of sensitive ink in a first color, which changes to a second color is the presence of chemical vapor or steam, and changes to a third color in the presence of ethylene oxide.

U.S. Pat. No. 5,344,017 shows another known sterilization pouch, in which the equivalent of sensor 520 is encased in a diamond shape formed by affixing the back to the front along lines forming a diamond.

FIG. 10 is a view of sterilization pouch 550. Sterilization pouch 550 is generally similar to pouch 500, and for brevity, only differences will be discussed.

Sterilization pouch 550 includes sensors 571, 572, 573 formed of thermally sensitive ink that changes color when different temperature thresholds $t_{571}$, $t_{572}$, $t_{573}$ are reached. Together, sensors 571, 572, 573 form an integrator. Sensors 571, 572, 572 are located behind panel 581, which ensures that the ink from the sensors does not contaminate the device being sterilized. In some embodiments, panel 581 is omitted. Panel 581 is typically transparent plastic.

Sterilization pouch 550 also includes sensors 574, 575, 576 that trigger when different temperature thresholds $t_{574}$, $t_{575}$, $t_{576}$ are reached. Sensors 574, 575, 578 are adapted to be read either electronically, magnetically or electromagnetically by an external sensor reader (see FIG. 2C). Sensors 574, 575, 578 are located behind panel 582, which ensures that the sensors remain separate from the device being sterilized.

Sterilization pouch 550 also includes PIT 590.

As used herein and in the claims, injector refers to a syringe or an auto-injector. A syringe is a device having a fluid and a hypodermic (hollow) needle wherein manual action of the user provides force for forcing the fluid through the hypodermic needle. An auto-injector is a device having a fluid, a spring and a hypodermic needle wherein the user merely places the device against his or her skin to activate the unit, thereby forcing the medicament, typically a fluid but sometimes a powder, through the hypodermic needle. In some instances, an auto-injector is an air-pressure driven gun that drives medicament through a device orifice into skin or onto a mucous membrane, without a needle. Auto-injectors are well known, for example, U.S. Pat. Nos. 5,092,843 and 5,354,286, having a common inventor herewith, the disclosure of which is hereby incorporated by reference. As used herein, an auto-injector includes a compressed gas driving mechanism, a battery powered mechanism, or other mechanism not limited to a spring.

In some situations, such as exposure to toxins, bee stings for persons allergic thereto, seizures or out-of-desirable-range levels of biomarkers, receiving an injection is critical for a person to stay alive. Persons at risk of such situations often carry an injector with them, since after realizing they have been exposed to danger, they have only a few moments of consciousness and so it is critical that an injector be nearby. In general, in a high threat situation with a rescue device, it is desirable for the rescue device, upon being used, to send a rescue signal indicating its location, so that rescue personnel can more readily know that their services are needed and find the harmed person. Additionally, for persons who should be carrying a rescue device, it may be desirable to remind such persons if their rescue device is not being carried, and/or if training is advisable. Similar considerations exists for caregivers of at-risk persons.

Figure 11A:
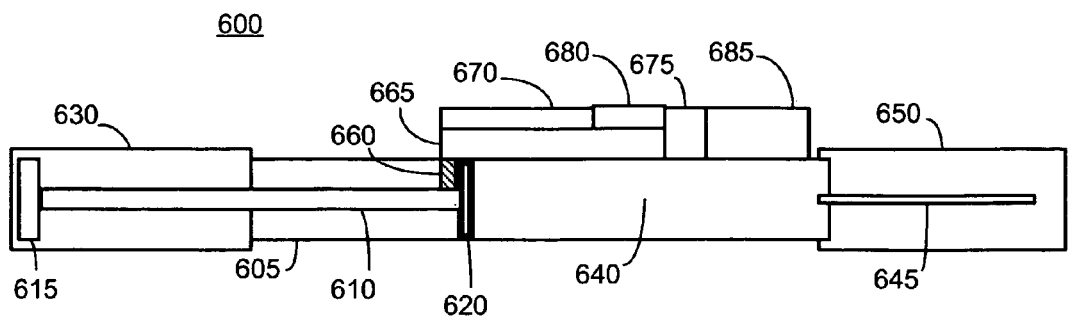
FIG. 11A-11B are views of injectors according to the present invention.

FIG. 11A is a side view of injector 600. Injector 600 is shown as a syringe but, in other embodiments, is an auto-injector. When injector 600 is used to dispense its dosage, it determines its location, and sends a message to a central facility, such as a rescue center or product management system 10, giving its unique identification number and its location. The central facility uses the unique identification number to determine the contents of injector 600 and thus what sort of threat may have occurred so that suitable rescue personnel may be dispatched. The unique identification number may also be associated with a likely user of the device, and the user's organization may be notified that a problem has occurred and help is on its way. Injector 600 is an embodiment of the configuration of FIG. 2F.

Injector 600 includes housing 605, stem 610, plunger 615, movable disc 620, end cap 630, dosage chamber 640, hypodermic needle 645, needle cap 650, sensor 660, processor with memory 665, communications interface 670, PIT 675, battery 680 and location interface 685. Dosage chamber 640 is at least partially filled with rescue fluid.

When a user feels the need for rescue fluid, the user removes end cap 630 and needle cap 650 from injector 600, inserts needle 645 into the user's skin, then presses plunger 615 towards housing 605. The force applied to plunger 615 is transmitted to disc 620 via stem 610. The movement of disc 620 towards needle 645 forces the rescue fluid through needle 645 and into the user.

Usage of an auto-injector is described in U.S. Pat. Nos. 5,092,843 and 5,354,286.

Sensor 660 is inside housing 605, and is triggered by the movement of disc 620. In some embodiments, sensor 660 is triggered by the movement of stem 610. When sensor 660 triggers, it provides a signal to processor 665 via magnetic coupling or a physical contact made through a hole in the wall of housing 605. Processor 665 activates location interface 685 to obtain the location of injector 600, such as global positioning system (GPS) coordinates. Processor 665 then activates communication interface 670, such as by initiating a cellphone call to a predetermined telephone number associated with a central facility, and when communications are established, provides a unique identification number stored in PIT 675 along with the location from location interface 685 and possibly a timestamp. In some embodiments, instead of using a voiceband cellular channel, communication interface 670 uses an emergency frequency or a control channel or another wireless channel. Battery 680 can be in a standby or non-use state until sensor 660 is triggered, and only needs to provide power for the aforementioned activities, so battery 680 can be small. In one case, disc 620 has a coating on its backside (side away from dosage chamber 640) that couples with sensor 660 to provide a first resistance to processor 665; when disc 620 is de-coupled from sensor 660 during use of injector 600, sensor 660 alone provides a second resistance to processor 665. The change in resistance, or the second resistance, seen by processor 665 serves as the trigger signal.

Figure 11B:
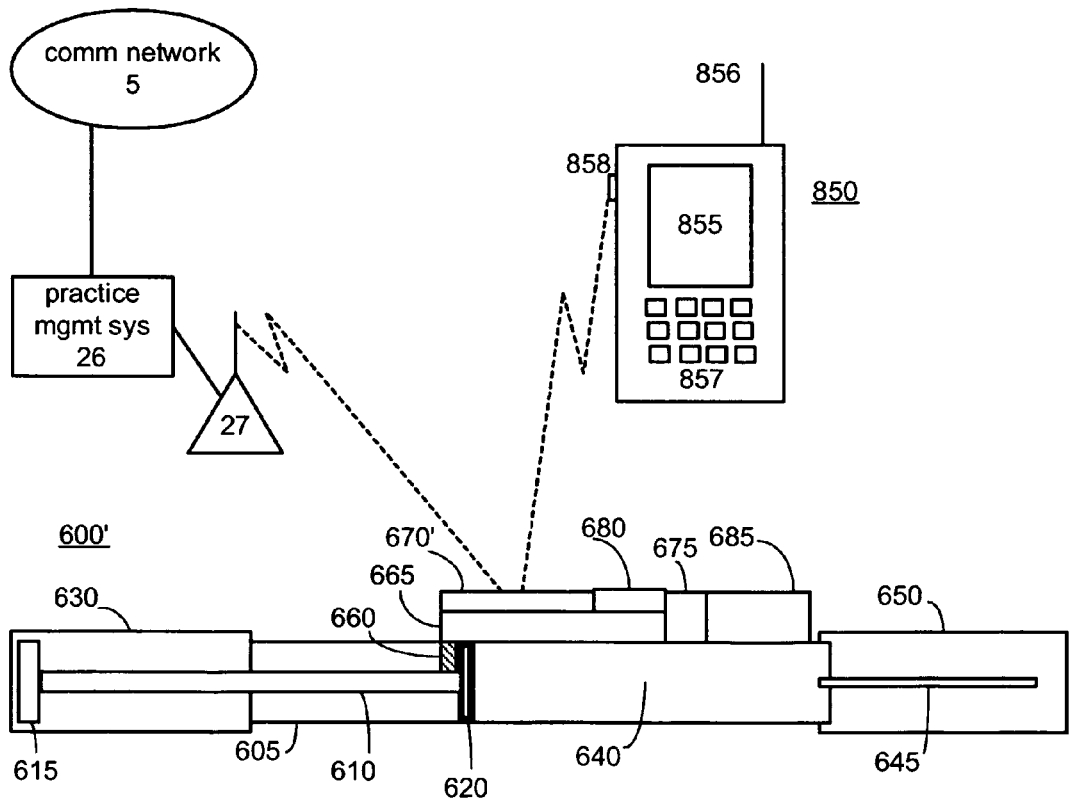

FIG. 11B shows injector 600' which is similar to injector 600 except that injector 600' is used with an external device, such as external device 850 or practice management system 26, having long-range communication capability and short-range communication capability, and possibly location sensing ability and image capture ability.

Device 850, such as a cellphone or personal digital assistant, has wireless communication ability, such as cellular, via antenna 856, ability to communicate with case 800 via interface 858 operative according to a short-range protocol (discussed below), a built-in GPS sensor (not shown), a built-in camera (not shown), display 855 and information entry means 857 such as a keypad.

Injector 600' includes communication interface 670' for communicating with device 850 via a suitable short-range communication protocol such as Bluetooth, WiFi or other local, preferably low-power, protocol. The communication protocol between injector 600' and device 850 enables injector 600' to (a) instruct device 850 to open a communication channel to the central facility, or other location, (b) send information to device 850 for relaying to the central facility, or other location, (c) instruct device 850 to display text on display 855, such as an instruction to a caregiver to take a picture then press * or to press # to begin and then end video streaming, (d) instruct device 850 to respond to events, such as depression of a * key, in a particular manner, and (e) instruct device 850 to transmit information such as its GPS coordinates to the central facility, or other location.

In some embodiments, injector 600' communicates with practice management system 26 instead of device 850. Practice management system 26 is similar to practice management system 25, discussed above, except that practice management system 26 has both long-range communication capability and short-range communication capability. System 26's short-range communication capability uses antenna 27 which operates according to a suitable short range protocol, such as Bluetooth or WiFi, to receive information from injector 600'. System 26's long-range communication capability is via connection to communication network 5, discussed above, which is one or more networks such as wireline or wireless data or voice networks.

In operation, injector 600' communicates information, such as its usage, to system 26 via antenna 27. System 26 then responds according to a predetermined procedure, such as alerting a private individual and/or placing a call to an emergency provider and so on. System 26 reports the location of injector 600' as being the location of system 26.

Figure 12A:
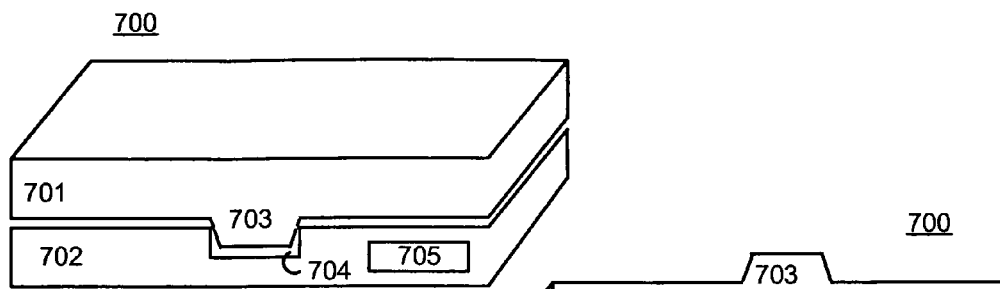
FIGS. 12A-12C are views of cases according to the present invention.

FIG. 12A shows the outside of case 700. Let it be assumed that case 700 holds a medical device or drug product, such an injector. In this embodiment, when the case is opened to remove the injector, the opening serves as the trigger signal to communicate at least one of the fact of opening, subsequent removal, subsequent usage, and location of case 700 to a central facility. Removal and use of an auto-injector can be sensed, for example, when case 700 has an audio sensor for detecting distinctive noises made by the auto-injector when it is removed and when it is used, particularly when the auto-injector is designed to produce such distinctive noises.

Case 700 includes lid 701, bottom part 702, top closure 703, bottom closure 704 and electronics 705. Electronics 705 incorporates PIT functionality, discussed above. When lid 701 is separate from bottom part 702, top closure 703 is separated from bottom closure 704. The separation is sensed by electronics 705, which obtains the GPS location of case 700 and its own self-stored identification code, and initiates communication with a central facility as discussed above.

In other embodiments, the case may contain multiple devices, such as injectors with different injectants, and when one of the devices is removed, the case communicates its location to the central facility and which device was removed. Other examples are pills, pills in a container that electrically communicates when the container is removed from the case, and a weight sensor for a multi-dose unit.

Figure 12B:
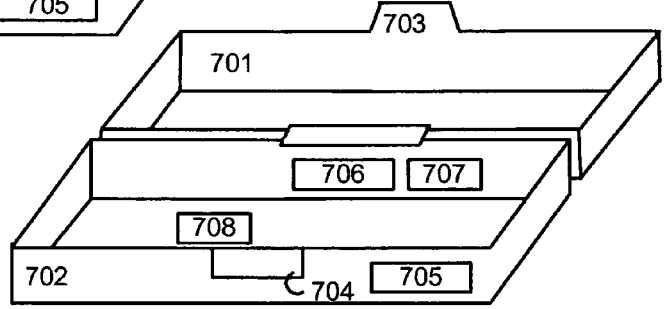

FIG. 12B shows the inside of case 700. Case 700 contains camera 706 and sensors 707, 708. Camera 706 transfers image information to electronics 705, which is able to receive, store and send the image information in association with other information such as GPS coordinates. Accordingly, an image can be sent to the central facility to assist in verifying that a device was used, and how much of a device was used. In some embodiments, camera 706 is positionable, such as by a caregiver, to provide a video picture or image stream of a removed auto-injector and/or the person having a problem.

Sensors 707, 708 are chosen from a thermal image sensor, a vibration sensor, a temperature sensor, a humidity sensor, a chemical sensor, an audio sensor and so on. There may be multiple instance of each of sensors 707, 708. Sensor 707 transfers information directly to electronics 705, while sensor 708 is observed by camera 706 which in turn provides an image of sensor 708 to electronics 705. For example, sensor 708 may be paper or ink that changes color when exposed to a particular substance or ambient condition. Accordingly, sensor readings can be sent to the central facility.

In some embodiments, instead of being used for individual items, case 700 serves as a shipping container. In these embodiments, case 700 may report to product management system 10 periodically, in response to requests, and/or when selected events occur.

Other emergency care devices or kits may be similar configured to report usage, such as a cardiac defibrillator, tracheotomy device, or emergency pharmaceuticals such as so-called heart clot busters: tissue plasminogen activator or streptokinase.

Any of the functions, such as sensing, reporting and alerting, discussed herein for an injector are also applicable to case 700, and vice-versa.

Figure 12C:
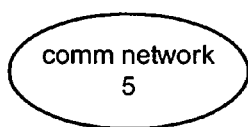
Figure 12C:
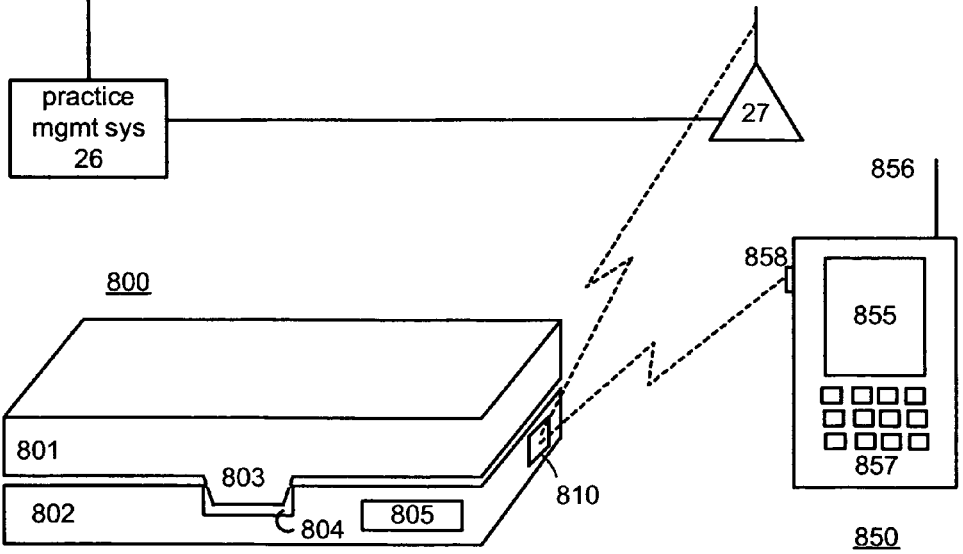
Figure 13A:
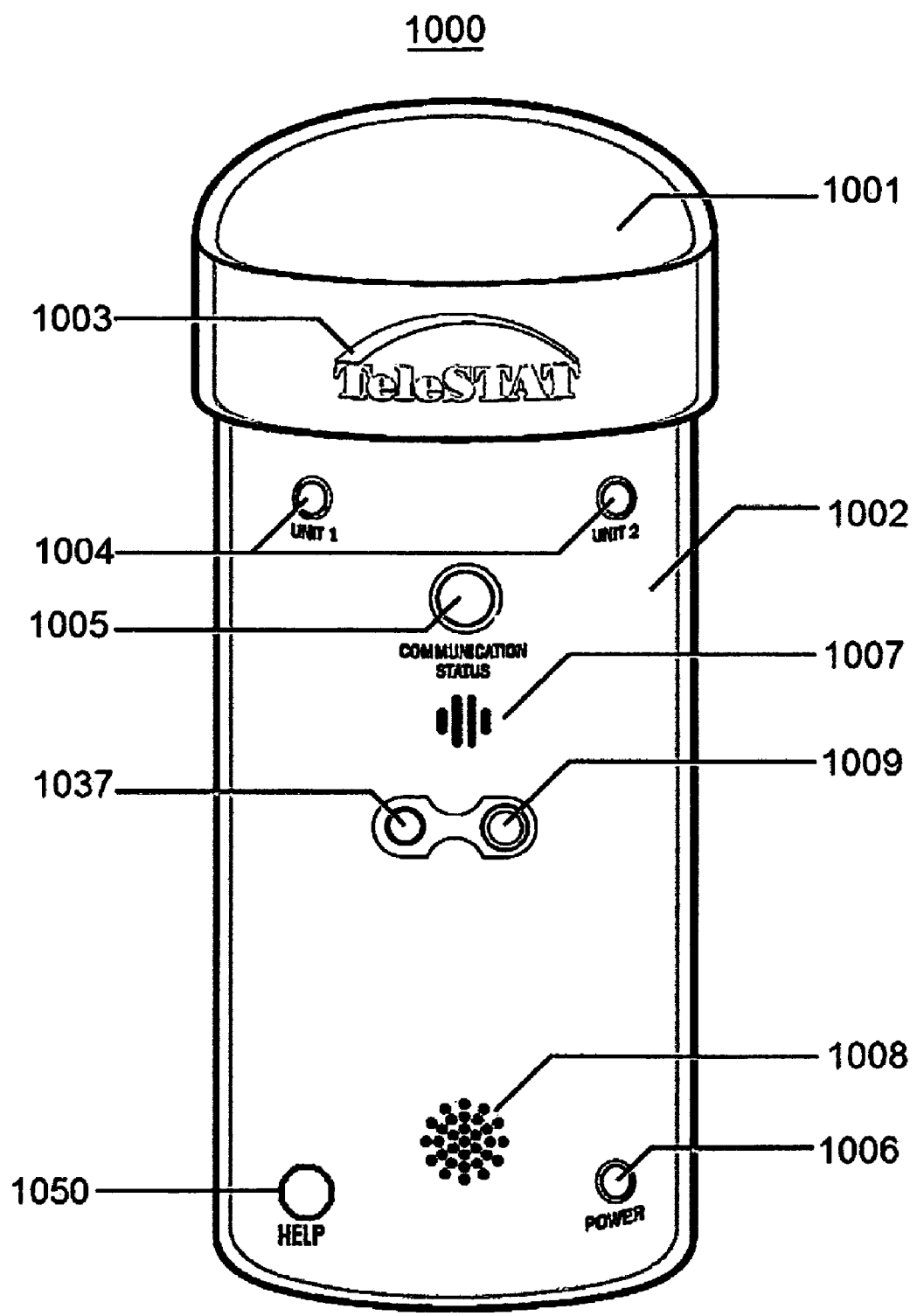
FIGS. 13A-13F are views of an another case according to the present invention.
Figure 13B:
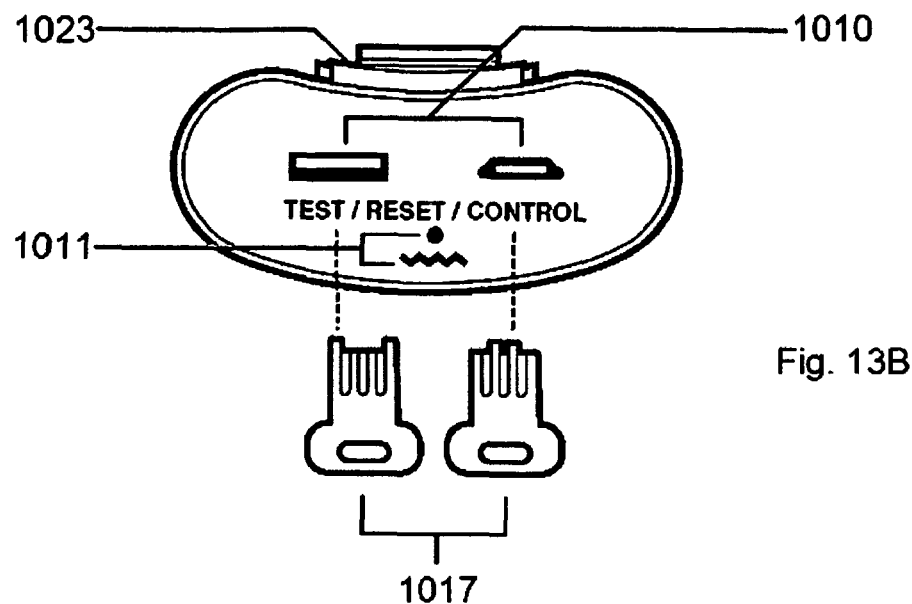
Figure 13D:
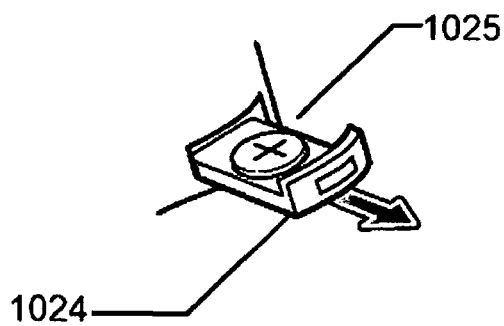
Figure 13E:
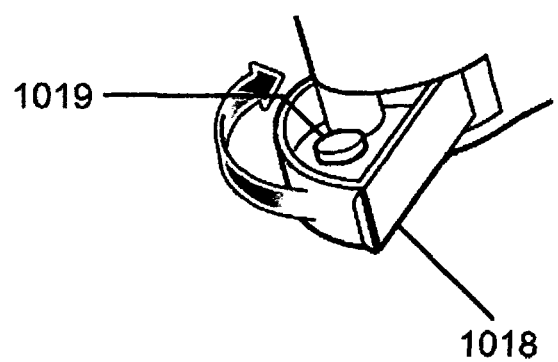
Figure 13C:
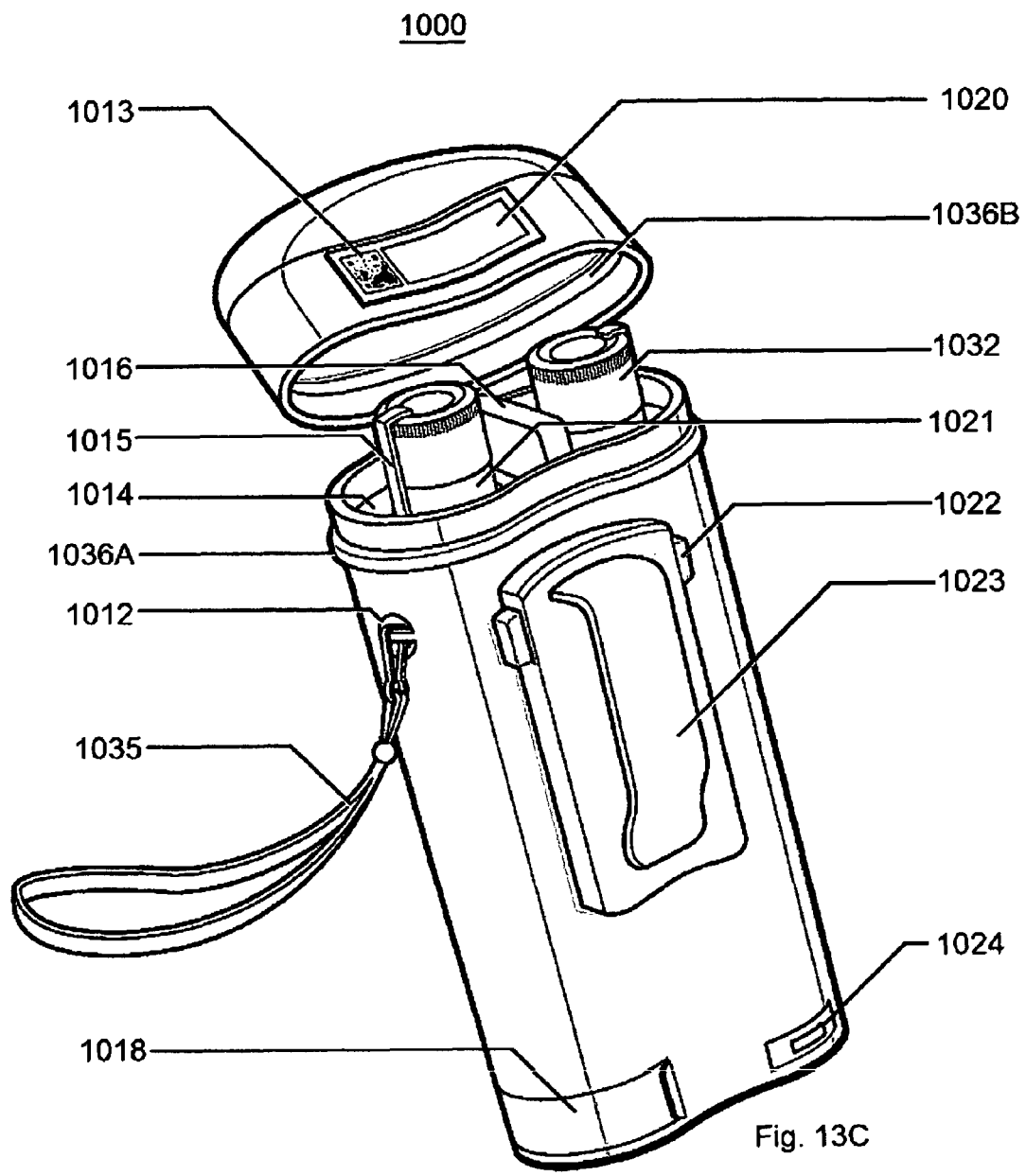
Figure 13F:
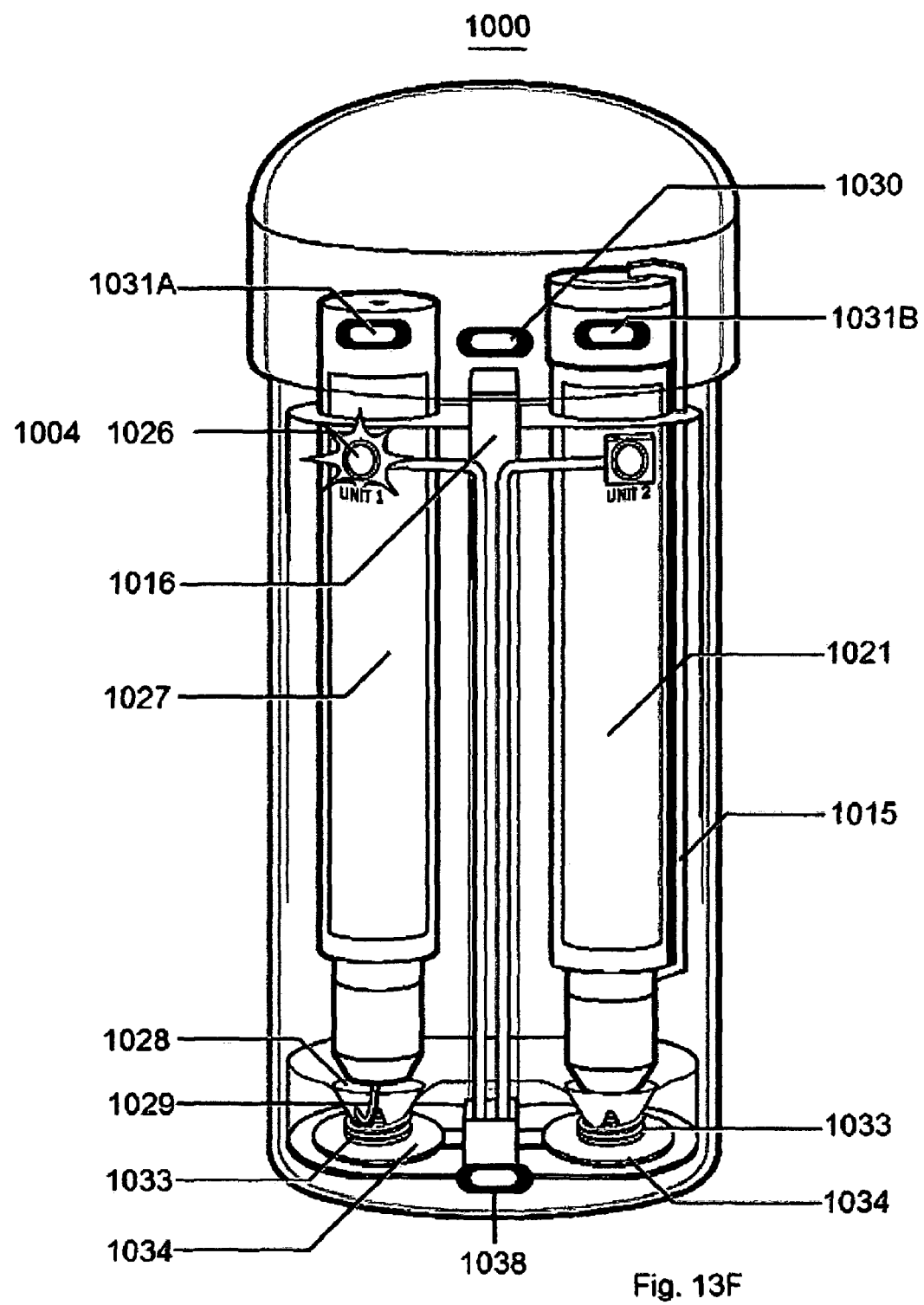

FIG. 12C shows case 800, which is similar to case 700, the differences being discussed below. Similarities are not discussed for brevity. Generally, case 800 functions in similar manner as case 700, except that case 800 uses features of an external device, such as external device 850 or practice management system 26. Device 850 and practice management system 26 are described above, during the discussion of FIG. 11B.

Case 800 includes communication interface 810 for communicating with device 850 via a suitable protocol such as Bluetooth or other local, preferably low-power, protocol. The communication protocol between case 800 and device 850 enables case 800 to (a) instruct device 850 to open a communication channel to the central facility, or other location, (b) send information to device 850 for relaying to the central facility, or other location, (c) instruct device 850 to display text on display 855, such as an instruction to a caregiver to take a picture then press * or to press # to begin and then end video streaming, (d) instruct device 850 to respond to events, such as depression of a * key, in a particular manner, and (e) instruct device 850 to transmit information such as its GPS coordinates to the central facility, or other location.

When the central facility is product management system 10, communication network 5 is the public switched telephone network coupled to the cellular telephone network that receives the call from processor 665 via communications interface 670. Communications interface 15 of product management system 10 serves to receive the call and store the event of the call in PIT database 50. PIT database 50 includes, in the record relating to the injector, the contents of the injector and an identity of a person having the injector. Rules database 85 includes a rule that when a call from injector 600 is received, an alert report is to be immediately prepared and delivered to analyst 90. In some embodiments, the rule or the database record relating to the injector specifies other parties that the alert report is to be delivered to, such as customer 20. Analyst 90 then arranges for dispatching of rescue personnel to the location of injector 600.

In some embodiments, rules database 85 includes rules for screening the situation, such as by a verification call to a person or device, or by inspecting an image or sensor reading, to minimize unnecessary dispatching of rescue personnel. The rules can be suggestions to analyst 90, automatically applied procedures executed by product management system 10, and any combination thereof.

In some embodiments, injector 600 is configured so that the central facility is alerted when injector 600 is not being carried by the user, and can contact the user, such as by telephone or email, to remind the user to carry injector 600. As used herein and in the claims, detecting usage of an injector encompasses detecting when fluid is being forced through the injector's hypodermic needle, and detecting when the device is or is not being carried by the user.

In some cases, injector 600 periodically reports its location to the central facility, either by initiating a location transmission or responding to a location poll from the central facility. The central facility then compares at least two successive location reports to determine whether injector 600 is moving. Lack of motion indicates that the user might have forgotten to carry the injector.

In some cases, injector 600 periodically checks its location, stores its current location, and compares at least one of its stored previous locations with its current location, and notifies the central facility only if the comparison indicates no change, that is lack of motion.

With respect to movement detection, the location sensor can use GPS coordinates or can use a local metric, such as the position of a drop of fluid in a chamber, or any other metric that changes based on movement of the injector.

Telemedicine, also known as telehealth, allows patients to connect remotely with healthcare providers. As used herein, the word "patient" includes a person suffering from a disease, an otherwise healthy person who has been subjected to a toxin such as an organophosphate poison, a clinical drug trial subject, a care giver, a good Samaritan, a first responder such as an emergency medical technician, and others who administer pharmaceuticals to themselves or others. Telemedicine programs can improve access to care, help to ensure more timely treatment, lower healthcare costs, improve outcomes for treatment, and improve the information available about the patient's disease state. Telemedicine programs may also be especially important for monitoring clinical trials. Some clinical trials necessary for regulatory approval of new medications require that the patient or a caregiver administer pharmaceuticals outside of a medical facility.

FIGS. 13A-13F, collectively referred to as FIG. 13, are views of case 1000 for containing pharmaceutical substances and for communicating with system 10. Case 1000 is similar to case 800, and only differences are discussed for brevity.

Case 1000 allows the patient to be connected with telehealth systems such as Lifeline® and others which are growing in popularity. Case 1000 and components thereof may be made of any suitable material, such as injection molded plastic, blow molded plastic, metal or other materials or combinations of materials. Case 1000 is generally rounded so that it is not snagged on other items. In other embodiments, case 1000 is kidney shaped so that one surface conforms to the contour of a body part such as the thigh, or chest wall. Other conforming shapes are also possible. A distinctive shape such the kidney shape or other shapes or textures can facilitate locating the case. This is important if the patient is visually impaired, working in a dark environment, or if the case is carried in a purse or backpack. One or more surfaces of case 1000 may be textured in a way to facilitate locating, orienting, or using one or more features of the case. Case 1000 may be waterproof when closed and designed to float when open or when closed. Case 1000 may protect the pharmaceutical container against any potentially harmful force, material or effect, such as mechanical shock, temperature, vibration, UV and other light, radiant energy, abrasion, piercing by sharp objects, tampering, contamination from dust, salt or moisture, which could cause the delivery system to become inoperable, or from biological contaminants which could infect the patient. Case 1000 may protect the patient or others from exposure to a toxic pharmaceutical in the case or the needle protruding from an expended autoinjector. An autoinjector is a spring-driven syringe Case 1000 may be hermetically sealed to maintain a controlled environment. A desiccant or other environmental control agent such as nitrogen may be placed inside case 1000. Case 1000 may contain one or more pharmaceutical containers, such as an autoinjector, a syringe, a vial containing liquid pharmaceuticals, an inhaler, or any of numerous types of containers for tablets, capsules, powders or ointments. In some embodiments, case 1000 include a cell phone or other communication device.

Pharmaceutical drugs deteriorate over time at a rate often correlated with their exposure to temperature. Outdated pharmaceuticals are not known to be effective and should be withdrawn when possible. The degradation products of some pharmaceuticals are toxic. The effect of high temperature exposure (such as might be encountered by patients carrying emergency use pharmaceuticals) on the pharmaceuticals and on container and closure systems of pharmaceuticals is often not well studied. Contaminants may be leached into the pharmaceutical.

Clinical trial pharmaceuticals may have only limited stability data necessitating a short time at given temperature exposures before the pharmaceuticals are replaced. It is especially difficult to follow the prescribed storage conditions for remotely administered pharmaceuticals. It is, therefore clear that both these classes of pharmaceuticals will benefit from the temperature recording capabilities of the case. This is especially important when the pharmaceuticals must be available in any environment where the patient travels.

In some cases it is important to document non-use. For example, if a patient claimed to have suffered injury from an event related to a given a pharmaceutical and the information provided by the case demonstrated that the pharmaceutical was not used as claimed by the patient; costly claims related to the purported injury could be avoided.

FIG. 13 shows cover 1001, body 1002, product name area 1003, pharmaceutical container status indicators 1004, communication status indicator 1005, power source status indicator 1006, speaker 1007, microphone 1008, camera lens 1009, device connections 101010, test/reset switch 1011, anchoring point 1012, bar code/RFID 1013, insert 1014, follower mechanism 1015, communication module 1016, keys 1017, secondary medication storage compartment 1018, secondary medication 1019, information label 1020, pharmaceutical containers 1021, detachment actuator 1022, removable belt clip 1023, power source compartment 1024, power source 1025, pharmaceutical container status indicator signaling needle exposed 1026, used pharmaceutical containers 1027, needle deflector 1028, needle 1029, sensor 1030 to signal opening of case 1000, sensor 1031 to signal presence or absence of pharmaceutical containers in case 1000, safety pin 1032, spring 1033, deflector sensor 1034, removable lanyard 1035, mating structures 1036, camera control 1037, environmental sensor 1038, and help button 1050.

Cover 1001 serves to protect the contents inside the case. Movement of cover 1001 may be sensed and become an event to be communicated. The cover 1001 may be slip off or hinged to the body 1002 of the case. The product name or other information 1003 may be engraved, embossed, or otherwise shown on the cover 1001, or elsewhere on the case. This feature and other such features may facilitate locating, orienting or using one or more features of the case. The cover 1001 may be opaque, translucent, or transparent. If transparent, the user would be able to visually inspect for the presence of a pharmaceutical container and be able to visually detect certain characteristics of the pharmaceutical containers.

A surface of the case which would be most readily visible, usually the front, or another surface may have indicators to inform the user or others of the status of the case or of the pharmaceutical containers 1021 inside the case. Communication status indicator 1005 shows, for example, whether the case is within range of the designated communications device or devices, signal strength, or whether the case is actively communicating with another device. Power source status indicator 1006 signals the strength or remaining life of a battery or other power source.

Pharmaceutical container status indicators 1004 provide information about individual pharmaceutical containers. For example a pharmaceutical container status indicator 1004 may show the presence or absence of a pharmaceutical container 1021 in a certain section of the case. The pharmaceutical container status indicator 1004 may also show that a pharmaceutical container 1021 has been removed and returned to the case or the physical characteristics of a certain pharmaceutical container 1021 are outside a specified range.

Communications status indicator 1005, pharmaceutical container status indicators 1004 and power source status indicator 1006 provides information through different light patterns (flashing or constant for example), through the use of multiple colors of lights, through the use of numeric displays, or other visual means. LEDs which consume low power exist in many colors.

Speaker 1007 delivers audible information. For example when the power is low, when the case is out of range of the designated communications device, or when live or recorded messages might assist the patient or others. Examples of messages and delivered audibly to the user include (i) a reminder to replace pharmaceutical container 1021 in case 1000, (ii) a notice that the contents of pharmaceutical container are about to expire and so should be replaced with a fresh batch, (iii) a notice that the user should look into an improved pharmaceutical, (iv) a notice that the manufacturer of pharmaceutical container 1021 has recalled its product;

some of these messages may be locally generated by case 1000 and some may be delivered from system 10.

Microphone 1008 allows the case to receive audible signals from the user or from a pharmaceutical container such as an autoinjector. It is known that various types of autoinjector may create a unique sound when activated. Alternatively, a pharmaceutical container 1021 might be designed to generate a unique sound to signal the case when the condition or location of the pharmaceutical container 1021 is changed in some way.

Camera lens 1009 attaches to a camera which may allow patient or others to record images to assist in diagnosing and treating the patient and in otherwise recording events related to the use of the pharmaceutical container 1021. Camera control 1037 allows the patient or others to activate and otherwise control the camera. Camera control 1037 may have a distinctive shape to allow the user to identify it. In some embodiments, the image is transmitted to a close-by communications device such as a cell phone. This will limit the cost of the case. In other embodiments, the case may have a monitor (not shown) on a surface of the case.

Device connections 1010 such as a USB port, a phone connection such as an RJ-11 jack, a connection to a wireless modem or other connection may be positioned on the bottom of the case or elsewhere. In certain embodiments, the device connections may be used to download or upload data or software from or to communications devices, other medical monitoring devices, computers, or other devices. In certain embodiments the device(s) connected to the case may be powered by the case; in others, the device(s) connected may power certain functions of the case; in others, the case could be used to connect two or more other devices. Examples of the devices which might be connected are cell phones, RF ID or barcode scanners, computers, transcutaneous stimulation devices to enhance absorption of pharmaceuticals, diagnostic devices such as electrocardiograph devices and peak flow meters, or others.

Test/reset/control switch 1011 is on the bottom of the case or elsewhere. This test/reset/control switch 1011 may be used to manually test, reset or control one or more functions of the case. In some embodiments, the switch may be accessed through the use of one or more specially shaped keys 1017, the shape of which will allow an individual with such a key to access the switch and activate certain functions of the test/reset/control switch 1011. In some embodiments, multiple keys each capable of activating different functions may be supplied for use with the case. In others, the test/reset/control switch is at the end of a hole through the case. In still other embodiments, there may be multiple configurations of two or more configurations of such test/reset/control switches 1011.

Removable belt clip 1023 or other such attachments may be mounted on the rear of the case or elsewhere on the case. In order to ensure that such an attachment remains firmly locked on to the case a positive mechanism may be used. Use of such a mechanism may necessitate use of a detachment actuator 1022.

Case 1000 has anchoring point 1012 for other attachments. These other attachments might include a removable lanyard 1035 as shown or others. Others might include a wrist strap, a belt clip, a pocket clip or others. A case may be supplied with an array of such attachments, one or more of which may be used by the patient or others.

The pharmaceutical container or containers 1021 carried in the case may be different depending upon the needs of the patient or other factors. Pharmaceutical container 1021 may come from the manufacturer with a barcode or RFID chip providing information such as NDC number and expiration date. Such information could be read by a scanner and entered into the communications module 1016. In order to facilitate use of the case with multiple types of pharmaceutical containers, the case may feature an insert 1014 made of a resilient or rigid material which conforms essentially to the shape of the pharmaceutical container or otherwise holds the container. The insert 1014 may be removable so that it could be replaced with another insert of the same or out a different type.

Case 1000 has communications module 1016 adapted to the requirements of the pharmaceutical product and in some cases to the requirements of the specific patient. The requirements for the communications module may change over time depending upon the pharmaceutical carried in the case and upon the individual patient. Many of the communications functions of the case are discussed above. The proximity of the case to another communications device can also be determined by another device or by the communications module. The communications module 1016 may be reprogrammed in situ, may be removed and modified by reprogramming or otherwise or may be replaced with a different communications module. The communications module 1016 may contain an active or passive RF ID chip. Such a chip would be read by a communications device such as a cell phone or another device. The RF ID chip in combination with the communications device can provide information as to the proximity of the case to the communications device. The communications module 1016 may be activated only when the case is opened or when other events occur, such as the expiration of a pharmaceutical, the removal of a pharmaceutical container 1021, the re-insertion into the case of a used pharmaceutical container 1021, a mechanical shock, or other event. The communications module may also be programmed to record events and to be active intermittently or constantly. The communications module 1016 may have a GPS chip mounted therein. The case may have a digital camera mounted therein. In other embodiments the communication module signals another communications device which has a GPS chip, digital camera, proximity sensing device or other capabilities. The communications module may also collect data from an environmental sensor 1038 inside the case, on the exterior of the case, or in other devices. Multiple sensors may be employed. The environmental sensor may be mounted so as to sense one or more conditions both inside and outside the case. The data may relate to environmental temperature, humidity, the condition of the patient and other variables. The communications module 1016 may store, analyze, and transmit the data automatically or as otherwise programmed. In one embodiment the communications module calculates the cumulative exposure to temperature in various ways. As an alternative a visually readable temperature indicator may be placed in or on the case.

In certain embodiments the power source is activated or the communications module is turned on either by the opening of the cover 1001, the removal of a pharmaceutical container 1021, altering the state of the test/reset/control switch 1011 or otherwise signaling a desire to activate the communications module.

Pharmaceutical containers 1021 may be of the EpiPen® type and are shown with a safety pin 1032 exposed after the case cover is lifted. It is known that removal of the safety pin 1032 arms the EpiPen autoinjector. In order to prevent premature arming, the case may be fitted with means to lock the safety pin 1032 in place while the injector is being removed from the case. This might be a follower mechanism 1015 which holds the safety pin 1032 in place until a sufficient portion of the autoinjector is available for grasping. Certain types of autoinjectors may not require a follower mechanism 1015 to keep the safety pin 1032 in place. Such a follower mechanism 1015 or other means could also be used to lock the pharmaceutical container into place. In the event such follower mechanisms were used to lock a pharmaceutical container 1021 into place, it might be unlocked through a signal from a communications device. To further assist in removal of the autoinjector or other pharmaceutical container 1021 an assist mechanism such as spring 1033, may be employed.

To seal the case, the body 1002 and cover 1001 may employ mating structures 1036 as shown. Other embodiments may include the use of a gasket either on the body 1002 or the cover 1001 or both.

To provide information visually or through electronically readable means, the case may feature an information label 1020 on the cover 1001 or elsewhere. This informational label may include a bar code/RFID 1013 such as a 2D bar code as shown. The informational label may include any other electronically readable tag instead of or in addition to the barcode/RFID 1013. The information label 1020 may contain information specific to the patient. The informational label 1020 may be of the self adherent type or may be carried in a pocket similar to the structure used to contain the address label carrying the address of the owner as is often used on luggage.

Power source 1025 could be a battery, a fuel cell or other such element for generating power. Power source 1025, may be rechargeable. The power source or an external power source attached to the device connections 1010 powers all components and functions of the case. In other embodiments, functions and recharging may be accomplished through the use of a docking station requiring no device connection 1010. This would be advantageous in order to insure that no liquid could penetrate the closed case.

Secondary medications 1019 would generally be tablets or other oral dosage forms. The secondary medications may be for use in association with the medication in the pharmaceutical container 1021. The secondary medication might be a medication to be used before or after use of the pharmaceutical container 1021. The secondary medication may be for use in treating the condition which necessitated the prescribing the medication in the pharmaceutical container 1021. In some situations a patient might carry an unrelated medication in the secondary medications compartment 1018.

The power source compartment 1025 and the secondary medication storage compartment 1018 may be mounted in a slidable, pivoting or other arrangement. In either case the compartments 1024, 1018 may have a locking function to avoid unwanted opening. In some cases it may be useful to send a signal to the communications module or otherwise when such structures are opened.

The pharmaceutical containers 1021 may be removed and replaced in the case. The case may feature a sensor 1030 to signal opening of case 1000, sensors 1031 to signal the presence or absence of pharmaceutical containers, environmental sensor 1038 to allow recording environmental variables. Sensors 1030, 1031, and 1038, speaker 1007, communications module 1016, status indicators 1005, 1006, and camera control 1037 may be powered by power source 1025 or by a power source connected to the case through the device connections. Information from the sensors may be stored in the communications module along with the time of the sensor reading. These variables may include freezing temperatures which exceeded a certain length of time, cumulative time at temperatures above a certain level, mechanical shock, relative humidity, environmental contamination in the area of the case and the patient, or other variables. Evaluation of these variables can be performed to assess the condition of the pharmaceutical containers 1021 and the products contained therein, the threat the environment poses to the patient, the need to move the patient out of the environment. These measurements could be used, for example, to calculate remaining shelf life of pharmaceutical containers 1021 subjected to unusual temperatures, to assess whether a pharmaceutical container 1021 had broken and allowed liquid to escape the pharmaceutical container 1021, to assess whether there was an unusual heat source such as a fire in the area of the case. When the pharmaceutical container is an autoinjector, returning the autoinjector to the case can be an important step to prevent injury resulting from contact with the exposed needle. It is important to know if a pharmaceutical container 1021 has been removed and returned to the case. When the pharmaceutical container is an autoinjector it is important to know if the autoinjector has been activated. A used pharmaceutical container 1027 of the autoinjector type is shown. In rare instances, autoinjectors may spontaneously activate. The patient may or may not replace the safety pin 1032 after activating an EpiPen autoinjector. The used pharmaceutical container 1027 is shown without a safety pin.

Needle deflector 1028 made of a material such as a metal and of a thickness which is not easily penetrated serves to deflect the needle 1029 which protrudes from the end of an autoinjector which has been activated. Needle deflector 1028 may be urged toward the autoinjector by spring 1033 as shown or another mechanism. When the needle of an autoinjector is protruding, the deflector will tend to force the needle to the side, thereby making the overall effective length of the autoinjector longer than the un-activated autoinjector. This difference and the absence of a safety pin 1032 could be visually observed through a clear cover 1001.

Alternatively, deflector sensor 1034 could sense needle 1029 contact with the needle deflector 1028 or displacement of the pharmaceutical container 1021 or the needle deflector; and signal the state of the autoinjector by changing the state of the pharmaceutical container status indicator. A structure similar to the needle deflector 1028 could also be used to sense the weight of the pharmaceutical container, signal an out of tolerance weight, and change the state of the pharmaceutical container status indicator. Spring 1033 may also facilitate removal of the pharmaceutical container after the cover 1001 is opened. This assumes that the combination of tolerances is such that the pharmaceutical container 1021 might compress the spring when the cover 1001 of the case is closed.

Help button 1050 enables the user of case 1000 to request communication with a central facility. To avoid accidental actuation, it is preferred that help button 1050 be recessed. Generally, there are three separate mechanisms for a user to request help; in some embodiments, a combination of these mechanisms are required. First, a user may speak a keyword or phrase into microphone 1008. Second, a user may press help button 1050. Third, a user may press test/reset switch 1011 in a distinctive pattern, such as a short press then a long press then a short press.

Usage examples will now be discussed.

The usage examples are directed to autoinjectors, but it should be understood that other pharmaceutical delivery vehicles are contemplated.

Reference to the service or system is understood to be system 10 as described above.

An example with Epinephrine will now be discussed.

Epinephrine packaged in an autoinjector is the standard of care for the severely allergic patient. Allergic reactions often progress from a mild reaction upon exposure to an allergen to a more severe reaction upon successive exposures. Severe allergic reaction often progresses to anaphylaxis. Anaphylaxis causes swelling of the airway and can result in suffocation and death. The need for immediate treatment with epinephrine is therefore evident. Some 4,000,000 autoinjectors filled with epinephrine are sold per year in the US. A small amount of epinephrine delivered rapidly can be life saving.

Studies show that patients and care givers are often not adequately trained to recognize anaphylaxis in the early stages of onset. Studies also show that, patients and caregivers are uncomfortable with how to use the autoinjector. The studies also indicate that the autoinjector is sometimes not readily available when needed. These results are reported even though there are numerous articles, websites, training devices, videos, and training courses which are offered by the autoinjector manufacturers, prescribing physicians, professional associations of allergists, lay associations of those suffering from allergies and interested parties, hospitals, schools, governmental organizations and others.

The patient and any care giver are under extreme stress at the time treatment of anaphylaxis is required. It is reported that the autoinjector is often not used when it should be. Sometimes the autoinjector is held inappropriately and activated in a way which leads to an injection into an unintended and/or inappropriate site. This can be an injection into the thumb, for example. Such an injection can itself lead to serious medical consequences including damage to the structure of the thumb. Injection in an inappropriate site will likely lead to failure to receive a dose of epinephrine as quickly or as large as would be the case if administered as specified into the anterior lateral thigh. Obviously, such a faulty injection will increase add to the already significant stress. In addition, delivery of a such a dose confounds decisions about follow on care. This is the case since the amount actually delivered cannot be easily determined.

After a single dose is delivered, another dose may be indicated if symptoms persist. From the above, it is clear that there is a significant benefit to having professional assistance in real time to provide guidance.

While the data are clear as to the benefits of epinephrine in the situation of anaphylaxis, there are side effects to the drug. Most are not severe, but some are sometimes sufficiently severe to require treatment. Side effects include palpitations, tachycardia, sweating, nausea and vomiting, respiratory difficulty, pallor, dizziness, weakness, tremor, headache, apprehension, nervousness, and anxiety.

Overdose may cause cerebral hemorrhage resulting from a sharp rise in blood pressure. Fatalities may also result from pulmonary edema because of peripheral vascular constriction together with cardiac stimulation.

Instructions for the EpiPen autoinjector approved by US FDA advise that the patient should call 911 and seek immediate medical attention after injecting. US FDA states that only related to anaphylaxis to food, there are 30,000 emergency room visits, 2,000 hospitalizations, and 150 deaths. The number and cost of 911 calls and ambulance transports related to food allergy is also significant. The number and cost emergency room visits, hospitalizations, deaths, 911 calls and ambulance transports related to hymenoptera sting and latex related anaphylaxis is still to be determined. The percentages in each category that have used an autoinjector are also still to be determined. It is clear that a system which allows medical personnel to intervene and better manage the remote emergency delivery of pharmaceuticals has significant benefit in avoiding unnecessary healthcare expense. Beyond the direct healthcare costs, the indirect cost of stress related disease, lost work and lost productivity is significant.

Other monitoring devices may be connected to the case to facilitate the actions discussed above.

Case 1000 and related systems can address the needs related to managing the treatment of anaphylaxis in the following ways:

Before treatment:
Enhance sense of confidence, empowerment and well being, Relief of anxiety regarding readiness to treat the allergic emergency.
Provide immediate, real time assistance in assessing the patient's condition.
Help to remind the patient or care giver to keep the autoinjector close.
Help the patient or care giver locate the autoinjector when needed.
Provide a means for contacting trained professionals for needed information before or during the onset of anaphylaxis.
Provide information on the expiration and storage of the autoinjector.
Help ensure outdated or recalled injectors are disposed of properly and replaced timely.
Provide a history of the interactions related to the patient and the autoinjectors prescribed to that patient.

At time of treatment:
Provide emergency voice, visual and data contact with trained professionals to assure proper treatment.
Help ensure that a second dosing is given when appropriate and not given when not appropriate.
Help reduce stress.
Record time, location, symptoms, changes in symptoms, adverse reactions, severity of reactions, and progress toward resolution of the anaphylaxis.
Secure professional recommendation for follow on treatment including deciding upon need to transport.

After treatment:
Document treatment and follow up.
Transmit to appropriate electronic medical records.
Ensure expended autoinjector is appropriately maintained and eventually disposed of to avoid injury to the patient or others.
Ensure that a replacement autoinjector is provided to the patient.
Ensure follow up as recommended is performed.
Ensure added training is offered if required.
Facilitate accumulation of data and analysis to aid in improving the products, services, training, readiness of responders, disease management for the patient and for the allergic population.

The following is an example of a use of the case containing epinephrine in an autoinjector. In this example, the EpiPen autoinjector is pharmaceutical container 1021. Nine year old Billy has a history of reaction to peanuts. The reactions have been becoming increasingly more severe. During the last reaction, Billy had an itch and a rash as before. He also had a little trouble catching his breath, but recovered after resting. Billy's Mom was very concerned and took Billy to an allergist after the last episode. The allergist advised that these types of reactions could progress and could be life-threatening. He described the symptoms and effects of anaphylaxis, showed Billy and his Mom how to use the EpiPen and prescribed the EpiPen for Billy. Billy's Mom had the prescription filled, and trained Billy on the use of the EpiPen. Still, she was concerned. She spoke with the school nurse and was glad that the nurse knew about the benefits of carrying the EpiPen. She was concerned when the nurse told her about another 9 year old who had injured another student, his best friend, while showing his EpiPen to him. She feared that Billy or his friends might play with the EpiPen in an inappropriate way. She was concerned that Billy might not have the EpiPen with him when a threatening allergic reaction occurred, that Billy might not recognize the onset of anaphylaxis in time to treat himself, might forget how to use the EpiPen and inject himself in his thumb, etc. She heard about a new system which offered a case for the EpiPen which could communicate with the same service her 70 year old Mother, Billy's Grandmother, Sara. Sara subscribed to the service monitor her heart rhythm. Sara had also fallen and fractured her hip. Billy's Mom added the service based on system 10 immediately to a family plan offered by the service.

The service provided case 1000 which communicated with Billy's cell phone and automatically communicated with the service when appropriate. For example, any time the cover 1001 of the case was opened or the pharmaceutical container 1021 (the EpiPen) was removed from the case, the communications module 1016 was activated and communicated with Billy's cell phone. The communications module 1016 in combination with the Billy's 3G GPS equipped cell phone was programmed to contact the service whenever the case was opened or a pharmaceutical container 1021 was removed. The opening of the case is sensed by sensor 1030 to signal opening of case 1000 when the cover 1001 is opened. The removal of a pharmaceutical container 1021 is sensed by sensor to signal presence or absence of pharmaceutical containers 31. When a pharmaceutical container 1021 is removed, pharmaceutical container status indicator 1004 associated with one of the two EpiPens Billy normally carried in the case changed from green to yellow. Communications module 1016, pharmaceutical container status indicator 1004 and sensors 1030, 1031 and 1038, speaker 1007, microphone 1008, status indicators 1005, 1006, and camera control 1037 are powered by power source 1025 or by a power source connected to the case through the device connections. Information from the sensors may be stored in the communications module along with the time of the sensor reading. When such events occurred Billy's cell phone sent the service information identifying Billy and his location. Under standing instructions, the service would then call Billy's Mom. Billy's Mom was now far more confident that her son would not be injured or die as a result of misuse, non use or abuse of the pharmaceutical container 1021 (the EpiPen).

The service contacted Billy on a schedule agreed upon by his Mom to provide refresher training. The case had been programmed with the expiration date of the pharmaceutical container 1021 (the EpiPen) when it was initially provided. This programming was performed using a barcode reader attached to the device connections 1010. Using this information, the service provides Billy's allergist and Billy's Mom a reminder to replace the EpiPen three weeks before the scheduled expiration.

Twice in the first month of his use of the service, when Billy forgot to put the EpiPen in his backpack, the service called his cell phone to remind him to get the EpiPen before he even left his house. This was because the communications module 1016 had been programmed to communicate when the case and Billy's cell phone became separated by a distance of more than 20'. As he went back into the house his cell phone was able to poll an RFID chip on the case to help Billy locate the case. Had he not been able to locate the case and remain within the specified distance; after a programmed time interval, the service and Billy's Mom would have been contacted.

About six months after Billy first received the case, he went to a birthday party. The hostess knew about Billy's allergies, and avoided serving peanuts. Unfortunately, some of the cookies imported from China were inadequately labeled and did not show that peanut flour was used in the manufacture. Billy ate the cookies and almost immediately developed a rash. He soon experienced a constriction of his airway.

Billy located the case in his overstuffed backpack by tactile sense. He immediately knew which end to open because the product name 3 was embossed on the cover 1001. Billy opened the case and removed the EpiPen. The follower mechanism 1015 helped to insure that the safety pin 1032 remained on the EpiPen and that the EpiPen was not inadvertently armed while removing it from the case. Once the EpiPen was removed from the case, the follower mechanism fell away. Billy removed the safety pin 1032 and injected himself with the EpiPen. Very quickly, his cell phone rang with a special ring tone indicating that the service was calling. By this time Billy had already successfully injected the epinephrine using the pharmaceutical container 1021. He was a little shaken, but answered the call. He passed the phone to the hostess. She spoke with the service and sent a photo of Billy to the service using his cell phone. The service called Billy's Mom and his allergist's emergency call line. It seemed that Billy was OK. The service advised how to monitor Billy's condition while a video consultation with the allergist could be arranged.

Billy placed the used pharmaceutical container 1027 (the activated EpiPen) back into the case so the now exposed needle 1029 would not present a potential hazard. When he did so, the needle 1029 was bent to the side by the needle deflector 1028. This caused the deflector sensor 1034 to signal pharmaceutical container status indicator 1004 to change to the color red.

Within a short time, Billy's symptoms had completely disappeared. The allergist decided that transport to the emergency room was not required. Billy's Mom arrived and drove Billy to the allergist's office. An exam confirmed that no further treatment was required. On the way home, Billy and his Mom stopped by their pharmacy to pick up a new EpiPen and have the case reprogrammed. The service sent a report to the allergist which the allergist placed in Billy's electronic medical record. This record was also sent to Billy's primary care physician.

The FDA approved labeling for the EpiPen states that after use, the patient or others should "Call 911 and seek immediate medical attention." This may result in the dispatch of an ambulance, transport, an emergency room admission and insurance claims for these events. In this example using the system avoided the potential for ambulance dispatch, transport, emergency room admission, and insurance claims processing for these events. The costs of these events depend upon the specifics of the situation including geographic location. The costs may reach thousands of dollars per event. Avoiding these costs and the stresses associated with emergency room visits is beneficial to the patient, caregivers, and society.

In another embodiment, the voice and video contact could be made using camera lens 1009, camera control 1037, speaker 1007, and microphone 1008 built into the case.

An example with clinical drug trials will now be discussed.

Clinical drug trials are necessary to secure approval from regulatory agencies for the marketing on new pharmaceuticals and new dosage forms for known pharmaceuticals. Clinical trials are expensive and notably difficult to manage. Clinical trials require that side effects and adverse reactions be recorded. Once a subject is enrolled in a clinical trial, it is important to ensure that data on each dosing is accurately and timely recorded. Failure to accurately record such data can lead to failure of the pharmaceutical to gain regulatory approval. Failure to capture results on any dosing may lead regulators to question the trial. Even if the regulators can be satisfied, failure to capture data will surely lengthen the clinical trial, increase the cost and delay time to market.

Some clinical trials require remote dosing over long periods of time, and dosing on the occurrence of some event such as at the onset of symptoms. In these cases, it is often not feasible to have the dose administered by a healthcare professional. In these cases, the dose must be administered by a care giver or the subject.

It is difficult to adequately train subjects and care givers to recognize symptoms in the early stages of onset of some conditions, to administer the pharmaceuticals in exactly the prescribed manner, and to fully and accurately record necessary information. Subjects and caregivers may be uncomfortable with some or many facets of the requirements. These facts are especially true if the study must run for long periods of time, if the study requires complex dosing or recordation, or if the dosing must be carried out in an emergency situation. Another factor which can confound such a trial is if the dose is not readily available when needed. This would result in a dose not being given when required, a dose delivered later that the optimal time, and a tendency to erroneously record information. In some cases, a dose might be delivered when not required or delivered multiple times when only one dosing is prescribed. Faulty dosing can itself lead to serious medical consequences including death. Such a faulty dosing can also add to the already significant stress. In addition, delivery of a faulty dose confounds decisions about follow on care and may jeopardize the acceptability of the trial.

Several clinical trials are underway or are likely for approval of new emergency pharmaceuticals and new delivery systems for existing pharmaceuticals. Some of these are life saving pharmaceuticals in autoinjectors. There is a growing regulatory emphasis on improving clinical trials, especially improving clinical trials of products to be used in pediatric patients.

There is a significant benefit to having professional assistance in real time to provide guidance. Without such assistance, advice that the patient should call 911 and seek immediate medical attention after the onset of certain side effects might be ignored. Alternatively, patients might seek treatment when not required.

Other monitoring devices can be connected to the case to facilitate the actions discussed above.

The case and related systems can address the needs related to managing clinical trials in the following ways:
Before dosing:
Enhance sense of confidence, empowerment and well being, Relief of anxiety regarding readiness to dose.
Provide immediate real time assistance in assessing the subject's condition.
Help to remind the subject or care giver to keep the dose close at hand.
Help the subject or care giver locate the dose when needed.
Provide a means for contacting trained professionals for needed information before or during dosing.
Provide information on the expiration and storage of the dose.
Help ensure that any outdated or recalled doses are disposed of properly and replaced timely.
Provide a history of the interactions related to the subject and the dose prescribed to that subject.
At time of dosing:
Provide emergency contact with trained professionals to assure proper dosing.
Help ensure that a second dosing is given when appropriate and not given when not appropriate.
Help reduce stress.
Record time, location, symptoms, changes in symptoms, adverse reactions, severity of reactions, progress toward resolution of any condition.
Secure professional recommendation for follow on treatment.
After dosing:
Document treatment and follow up.
Transmit to appropriate electronic medical records.
Ensure expended container is appropriately maintained and eventually disposed of.
Ensure that a replacement dose is provided to the subject.
Ensure follow up as recommended is performed.
Ensure added training is offered if required.
Facilitate accumulation of data and analysis to aid in completing the clinical trial, improving the protocol or the products, services, training, disease management for the subject and for the population which is the subject of the clinical trial.

The following is an example of a use of the case containing diazepam in an autoinjector hereafter called the DIAPen that is pharmaceutical container 1021.

Diazepam is the accepted standard of care for severe epileptic seizure. Diazepam is a controlled drug because of the potential for abuse. The only parenteral route of administration approved for civilian self administration diazepam is the rectal route. Rectal administration is an embarrassment for some people. The absorption of rectal diazepam into the bloodstream is erratic. In this example, XYZPHARM has been authorized to run a clinical trial on diazepam in an autoinjector. XYZPHARM hopes to market the diazepam autoinjector as an improvement over the rectal dosage form.

Fourteen year old JJ has a history of seizure. His seizures are infrequent, but severe. Before being enrolled in the XYZPHARM clinical, JJ was walking in a crowd with his Mom on a busy New York street. He dropped due to a seizure and only recovered when rectal diazepam was administered. While JJ's Mom was administering the rectal diazepam, a crowd gathered to watch and someone in the crowd stole her purse. This was a very traumatic event.

JJ's Mom was very pleased when presented with the opportunity to enroll in the XYZPHARM clinical after the last episode. The only way to run such a clinical is to have caregivers trained to administer diazepam at the onset of a seizure. The XYZPHARM study coordinator carefully trained JJ and all his care givers in how to avoid the potentially life-threatening issues related to seizure. He described the symptoms and affects of seizure, showed JJ and his caregivers, including the school nurse, how to use the DIAPen. The school nurse knew about the benefits of carrying the DIAPen since she had been an Army medic and knew of the military version of the DIAPen. Still, everyone was duly concerned when the nurse discussed the story about 9 year old who had injured another student, his best friend, while showing a similar product, the EpiPen to him.

The study coordinator was able to allay their concerns when he discussed the case and system which would be used to help manage the clinical. He described and demonstrated the case and system and all their functions in detail. He discussed the fact that each DIAPen provided would come in a case which would transmit its location to the clinical monitoring site every 15 minutes until opened, when opened and when the pharmaceutical container 1021 (the DIAPen) was removed from the case. The study coordinator explained that he case automatically communicated with the clinical monitoring site at regular programmed fifteen minute intervals, when the caregiver wished to ask a question or receive added training, when an event such as dropping the case onto a concrete floor occurred. For example, any time the cover 1001 of the case was opened or the pharmaceutical container 1021 (the DIAPen) was removed from the case, the communications module 1016 was activated and communicated with the clinical monitoring site. The 3G GPS equipped communications module 1016 was programmed to contact the service whenever the case was opened or a pharmaceutical container 1021 was removed. The opening of the case is sensed by sensor 1030 to signal opening of case 1000 when the cover 1001 is opened. The removal of a pharmaceutical container 1021 is sensed by sensor to signal presence or absence of pharmaceutical containers 31. When a pharmaceutical container 1021 is removed, pharmaceutical container status indicator 1004 associated with the DIAPens which JJ and his care givers normally carry in the cases changes from green to yellow. Communications module 1016, pharmaceutical container status indicator 1004 and sensors 1030 1031 and 1038, speaker 1007, microphone 1008, status indicators 1005, 1006, and camera control 1037 are powered by power source 1025 or by a power source connected to the case through the device connections. Information from the sensors may be stored in the communications module along with the time of the sensor reading.

When events such as the opening of the case occurred, the case sent the clinical trial monitoring site sent signals identifying JJ and his location. Under standing instructions, the clinical monitoring center would then call JJ's Mom. JJ's Mom was now far more confident that her son would not be injured or die as a result of misuse, non use or abuse of the pharmaceutical container 1021 (the DIAPen).

JJ's caregivers understood the benefits of the case since they had exposure to similar technologies in their homes and automobiles: GPS, internet access, cell phones with video capabilities, health monitoring devices which could automatically dial healthcare systems, etc. The study coordinator described how various other monitoring and communications devices could be connected using the device connections 1010. The study protocol specified that as soon as the diazepam injection was given, the caregiver should plug a video recorder provided by XYZPHARM into case 1000 and record JJ's condition for 15 minutes. The study coordinator advised that, depending on JJ's medical responses, the protocol might require that other devices such as blood pressure monitors be used. These could also be attached to the case using the device connections.

The clinical monitoring center contacted JJ and the care givers on a schedule through a cell phone integrated into the communications module 1016 to provide refresher training. Since the case had been programmed with the expiration date of the pharmaceutical container 1021 (the DIAPen) when it was initially provided, the service provides JJ's caregivers a reminder to replace the DIAPen three weeks before the scheduled expiration.

During the first month of his enrollment in the clinical trial one of JJ's caregivers forgot to put the DIAPen in his backpack, the case signaled him to remind him to get the DIAPen before he even left his house. This was because the communications module 1016 had been programmed to communicate when the case and the caregiver's key ring became separated by a distance of more than 20'. As he went back into the house the case was able to poll an RFID chip on the key ring to help JJ's caregiver locate the case. Had he not been able to locate the case and remain within the specified distance; after a programmed time interval, the clinical trial monitoring center would have been contacted.

About six months after JJ first received the case; he suffered a seizure and fell to the ground, striking his head as he fell. JJ's caregiver opened the case and removed the DIAPen. The follower mechanism 1015 helped to insure that the safety pin 1032 remained on the DIAPen and that the DIAPen was not inadvertently armed while removing it from the case. Once the DIAPen was removed from the case, the follower mechanism fell away. JJ's caregiver removed the safety pin 1032 and injected him with the DIAPen. Very quickly, the case rang with a special ring tone indicating that the clinical monitoring center was calling. By this time JJ's caregiver had already successfully injected the diazepam using the pharmaceutical container 1021. He was a little shaken, but answered the call and attached the video camera. The caregiver spoke with the clinical monitoring center and sent a video of JJ to the service using the 3G cell phone integral to the communications module 1016. The clinical monitoring center observed that while the seizure appeared to be resolved JJ remained unresponsive and that he began bleeding from his head. The clinical monitoring center called 911, provided JJ's location, a professional description of his symptoms and transmitted a video clip of JJ's head trauma. The clinical trial monitoring center advised the caregiver how to attend to JJ while waiting for the paramedics to arrive. The caregiver placed the used pharmaceutical container 1027 (the activated DIAPen) back into the case so the now exposed needle 1029 would not present a potential hazard. When he did so, the needle 1029 was bent to the side by the needle deflector 1028. This caused the deflector sensor 1034 to signal pharmaceutical container status indicator 1004 to change to the color red.

When the paramedics arrived they adjudged that JJ's head trauma required immediate transport. At the hospital, JJ was treated for concussion and his head stitched. After JJ was released, the caregiver was provided with a new DIAPen and his case reprogrammed. The clinical monitoring center prepared a full report for the clinical trial records and sent a report to JJ's primary care physician which he placed in JJ's electronic medical record.

The FDA requires that the sponsors of clinical trials keep full and accurate records of their clinical trials. There is great emphasis on insuring that any trials involving children be well run. In this example using the system avoided the potential for error and misunderstanding in administering and recording the results of each dosing. The costs of such errors and misunderstandings depends upon the specifics of the situation. It may be that only a small number of errors are made during a clinical. In that event, only a few dosings might have to be eliminated from the analysis. The more dosings which are eliminated or not given, the longer the clinical trial must run. The longer the clinical trial runs, the longer the delay in time to market. If many errors are made, the FDA may find the entire clinical trial unacceptable. The costs may reach millions of dollars. Avoiding these costs and the delay in introducing improved new medications is beneficial to the sponsors of the clinical, the patient, caregivers, and society.

In this specific instance the system provided benefits in the treatment of a medical condition unrelated to the particular clinical trial. It is known that severe brain injury should be treated as rapidly as possible to avoid permanent, irreversible brain damage.

An example with antidotes for organophosphate poisoning will now be discussed.

Antidotes packaged in an autoinjector are the standard of care for organophosphate poisoning. Such autoinjectors have been stockpiled for use. Workers manufacturing pesticides, military personnel, emergency responders, and, in the event of a terrorist event, civilians may suffer organophosphate poisoning. Organophosphate poisoning causes deterioration of the nervous system. Control of respiration and other functions is compromised. Organophosphate poisoning can result in rapid death. The need for immediate treatment with is therefore evident. A small amount of antidote delivered rapidly can be life saving. The side effects of antidote alone cause debilitation. Medical treatment after organophosphate treatment is mandatory. Medical treatment after administering the organophosphate antidote is highly desirable even if the patient has not suffered organophosphate poisoning.

At risk populations are often not adequately trained to recognize the symptoms of organophosphate poisoning in the early stages of onset. Information from Israel during the first Gulf War showed that patients and caregivers are uncomfortable with how to use the autoinjector. These results were reported even though there were numerous articles, training devices, videos, and training courses which are offered by the Israeli government and other interested organizations. Ensuring that the autoinjector is readily available when needed is problematic.

The patient and any care giver are under extreme stress at the time treatment of organophosphate poisoning is required. Sometimes the autoinjector is held inappropriately and activated in a way which leads to an injection into an unintended and/or inappropriate site. This can be an injection into the thumb, for example. Such an injection can itself lead to serious medical consequences including damage to the structure of the thumb. Injection in an inappropriate site will likely lead to failure to receive the dose of antidote as quickly as would be the case if administered as specified into the anterior lateral thigh. Obviously, such a faulty injection will increase add to the already significant stress. In addition, delivery of a such a dose confounds decisions about follow on care. This is the case since the amount actually delivered cannot be easily determined.

After a single dose is delivered, another dose may be indicated if symptoms persist. Again, there is a benefit to having professional assistance in real time to provide guidance.

While the data are clear as to the benefits of antidotes in the situation of organophosphate poisoning, there are side effects to the drug. The side effects are often sufficiently severe to require treatment.

There may be sensors in place to monitor the presence and type of toxins in the environment. However, these sensors do nothing to advise how many individuals have administered antidote, where and when.

Other monitoring devices may be connected to the case to facilitate the actions discussed above.

The case and related systems can address the needs related to managing the treatment of organophosphate poisoning in the following ways:

Before treatment:
Help manage resources such as first responders. This would include dispatch of resources to the patient.
Enhance sense of confidence, empowerment and well being, Relief of anxiety regarding readiness to treat the emergency.
Provide immediate, real time assistance in assessing the patient's condition.
Help to remind the patient or care giver to keep the autoinjector close.
Help the patient or care giver locate the autoinjector when needed.
Provide a means for contacting trained professionals for needed information before or during the onset of symptoms.
Provide information on the expiration and storage of the autoinjector.
Help ensure that any outdated or recalled doses are disposed of properly and replaced timely.
Provide a history of the interactions related to the patient and the autoinjectors prescribed to that patient.

At time of treatment:
Help ensure that others do not inappropriately administer antidote or otherwise act inappropriately.
Provide emergency contact with trained professionals to assure proper treatment.
Help ensure that a second dosing is given when appropriate and not given when not appropriate.
Help reduce stress.
Record time, location, symptoms, changes in symptoms, adverse reactions, severity of reactions, progress toward resolution of the symptoms.
Secure professional recommendation for follow on treatment including deciding upon need to transport.
Assist in planning and resourcing further casualty management.

After treatment:
Document treatment and follow up.
Transmit to appropriate electronic medical records.
Ensure expended autoinjector is appropriately maintained and eventually disposed of to avoid injury to the patient or others.
Ensure that a replacement autoinjector is provided to the patient.
Ensure follow up as recommended is performed.
Ensure added training is offered if required.
Facilitate accumulation of data and analysis to aid in improving the products, services, training, readiness of responders, casualty management for the patient and for the at risk population.

The following is an example of a use of the case containing atropine in an autoinjector hereafter called the AtroPen that is pharmaceutical container 1021. Atropine packaged in an autoinjector is the accepted standard of care for organophosphate poisoning. Atropine is a prescription drug with the potential for significant side effects. In the treatment of organophosphate poisoning it is important to have rapid treatment. If not treated organophosphate poisoning can lead to death in minutes. PESTCHEM produces pesticides most of which have organophosphates as the active ingredient. PESTCHEM has a sophisticated safety plan which includes sensors to detect any discharges of the deadly chemicals they process, use of gas masks, frequent training, hazmat labeling, and atropine autoinjectors housed in a cases which some workers carry and which are stored in strategic locations around the five acre production site for emergency use.

PESTCHEM had one incident 20 years ago wherein an employee died from organophosphate poisoning. Long before the incident, all employees were well trained to administer atropine at the onset of a organophosphate poisoning. Even though the deceased employee did not follow a number of PESTCHEM's safety regulations and was arguably grossly negligent; PESTCHEM settled the wrongful death claim for an undisclosed sum believed to be over $3,000,000.

PESTCHEM significantly upgraded their procedures after settling the suit. PESTCHEM tried to determine the best way to avoid a recurrence, but found that there was no technology which was adequate to help them manage emergencies to their complete satisfaction. PESTCHEM can now use a system which provides much information needed to help avoid a recurrence of injury and to provide assistance when an emergency occurs.

The PESTCHEM safety officer carefully trains all employees in how to avoid the potentially life-threatening issues related to organophosphate poisoning. He described the symptoms and affects of organophosphate poisoning, showed employees, including the senior managers, how to use the AtroPen. The Manufacturing vice president knew about the benefits of carrying the AtroPen since she had been an Army medic and knew of the military version of the AtroPen. Still, everyone was highly concerned at the thought of facing an incident and injecting themselves.

The safety officer is now able to allay their concerns when he discusses the system which would be used to help manage any incident which might occur. He describes and demonstrates all functions of the AtroPen, the case and system in detail. He discusses the fact that each AtroPen provided would come in case 1000 which would transmit its location to the clinical monitoring site every 15 minutes after case 1000 was opened and pharmaceutical container 1021 was removed from case 1000. He covers the facts that employees and first responders would be assisted by the features of the case and system. He explains that he case automatically communicates with the safety monitoring center at regular programmed fifteen minute intervals, when the employee signals that he wishes to ask a question or receive added training, when an event such as dropping the case onto a concrete floor occurs. For example, any time the cover 1001 of the case is opened or the pharmaceutical container 1021 (the AtroPen) is removed from the case, the communications module 1016 is activated and communicates with the safety monitoring center. The 3G GPS equipped communications module 1016 is programmed to contact the service whenever the case is opened or a pharmaceutical container 1021 is removed. The opening of the case is sensed by sensor 1030 to signal opening of case 1000 when the cover 1001 is opened. The removal of a pharmaceutical container 1021 is sensed by sensor to signal presence or absence of pharmaceutical containers 31. When a pharmaceutical container 1021 is removed, pharmaceutical container status indicator 1004 associated with the AtroPen changes from green to yellow. Communications module 1016, pharmaceutical container status indicator 1004 and sensors 1030, 1031 and 1038, speaker 1007, microphone 1008, status indicators 1005, 1006, and camera control 1037 are powered by power source 1025 or by a power source connected to the case through the device connections. Information from the sensors may be stored in the communications module along with the time of the sensor reading. When selected events, such as opening cover 1001 of case 1000, occur the case sends the safety monitoring center a signal identifying the nearest employee to the case and the location of the case. This is possible because each employee wears a badge which contains an active RFID chip. Under standing instructions, the safety monitoring center would then call employee's supervisor. Management was now far more confident that employees would not be injured or die as a result of misuse, non use or abuse of the pharmaceutical container 1021 (the AtroPen).

Employees understood the benefits of the case since they had exposure to similar technologies in their homes and automobiles. The safety officer described how various other monitoring and communications devices could-be connected using the device connections 1010. The safety protocol specified that as soon as the atropine injection was given and the employee was in an environment known not to be contaminated, the employee or first responder should plug a heart rate monitor provided by PESTCHEM into the case, attach the sensor of the heart rate monitor to the employee's finger and record employee's condition for 15 minutes. The safety officer advised that, depending on employee's medical responses, the protocol might require that other devices such as a video camera be used. These could also be attached to the case using the device connections.

The safety monitoring center contacted employees on a regular schedule through a cell phone integrated into the communications module 1016 to remind them to attend refresher training. Since the case had been programmed with the expiration date of the pharmaceutical container 1021 (the AtroPen) when it was initially provided, the service provides employees a replacement AtroPen one week before its scheduled expiration.

During the first month of use of the system, one of employees forgot to put the AtroPen on his belt, the case signaled him to remind him to get the AtroPen before he even left the changing room. This was because the communications module 1016 had been programmed to communicate when the case and employee's badge (both of which contained RFID chips) were not read together when the employee passes one of the readers located throughout the PESTCHEM site. PESTCHEM had placed such readers at the exit of each changing room. Had he not been able to locate the case and left the changing room without it, the safety officer would have been contacted.

In one instance, the environmental sensor 1038 detected a sudden rise in the temperature of a case which was stored in a sensitive area of the PESTCHEM factory. The safety officer sent a first responder to the site of the case. The first responder discovered that a small fire had broken out in a heater for one of the mixing vessels. Had this gone undiscovered it could have resulted in a Bhopal-like event. As it was, the fire was quickly extinguished with no release of toxic materials.

About six months after employees first received the case; there was an accidental release, a spill, of one of the organophosphate compounds. Sensors near the spill detected the spill and recorded warnings near the release sounded loudly. The accidental release was small and an employee acted quickly to isolate the spill. The warnings, however, were heard by a number of employees, some of whom were not near the spill. Seven employees in three separate locations opened the case and removed the pharmaceutical container 1021 (the AtroPen). The follower mechanism 1015 helped to insure that the safety pin 1032 remained on the AtroPen and that the AtroPen was not inadvertently armed while removing it from the case. Once the AtroPen was removed from the case, the follower mechanism fell away. Each of the seven employees removed the safety pin 1032 and injected himself with the AtroPen. Very quickly, the safety monitoring center realized that there were seven employees in three locations who had needlessly injected themselves. In order to manage the side effects of atropine each of the employees needed medical attention. This was also prudent to insure that no other employees injected unless there were some real need to do so. The safety officer feared that, in such a stressful situation, some employees might confuse the side effects of atropine which their colleagues were experiencing with organophosphate poisoning. Because the case had transmitted information on which employees had injected and their locations, the safety officer was able send available first responders quickly to the employees most at risk, to plan the routes of the first responders so they avoided the area of the initial spill until the atropine casualties were attended to. The safety officer called 911, gave a professional situation report and asked that they dispatch two paramedic units as a precaution. The first responders spoke with the safety monitoring center and sent voice messages and a video of each of the seven employees and the three sites to the safety officer using the video equipped 3G cell phone integral to the communications module 1016. The safety monitoring center followed the progress of the first responders as they moved all seven employees to the executive conference room which had been converted to a casualty center in accordance with the safety plan. Paramedics were on scene in the casualty center within minutes to treat the atropine casualties. The first responders placed the used pharmaceutical container 1027 (the activated AtroPen.) back into the case so the now exposed needle 1029 would not present a potential hazard. When he did so, the needle 1029 was bent to the side by the needle deflector 1028. This caused the deflector sensor 1034 to signal pharmaceutical container status indicator 1004 to change to the color red.

The paramedics treated each employee. One required transport to the hospital. He was a 59 year old employee with no prior reported history of cardiovascular disease who may have suffered a coronary event. After all employee atropine casualties were treated, the safety officer reset the case using three special keys 1017 which he inserted into the test/reset/control switch 1011 of each case; placed a new AtroPen in each case and reprogrammed the case with the expiration using a bar code scanner. The safety monitoring center prepared a full report for the safety records and sent a report to each employee's record and, under employees' standing permission, to each employee's primary care physician which he placed in employees's electronic medical record.

Various agencies such as OSHA, EPA and local agencies require that the employers keep full and accurate records regarding safety matters. There is great emphasis on ensuring that any facilities such as PESTCHEM which use or produce toxic materials are well controlled. In this example using the system avoided the potential for error and misunderstanding in managing the emergency situation and recording the results of those efforts. The costs of such errors and misunderstandings depends upon the specifics of the situation. It may be that a single, small error is made. Even one such error can result in an expensive lawsuit. The more errors, the greater the chances for claims, higher premiums, regulatory citations and fines. If many errors are made, the regulatory authorities may find the entire facility unacceptable. The costs may reach millions of dollars and even lead to bankruptcy. Avoiding the possibilities for injury and these costs is beneficial to industry, employees and society.

The larger the site and the greater the number of casualties, the greater the potential benefit of the system. Certain individuals such as first responders and those responsible for managing emergencies could benefit greatly from being equipped with the system.

A usage example with an asthma inhaler will now be discussed.

Asthma is one of the most common chronic diseases of childhood affecting an estimated 6 million children. Asthma is often a disease for life. It is controlled rather than cured. Several classes of drugs are used to control asthma. Short acting beta agonist (SABA), long acting beta agonist (LABA) and inhaled corticosteroids (ICS) are pharmaceuticals often packaged in inhalers. The generally preferred choices for the standard of care are as follows: For intermittent asthma: SABA; For persistent asthma step 2: low dose ICS; For persistent asthma step 3: low dose ICS plus LABA; For persistent asthma step 4: medium dose ICS plus LABA; For persistent asthma step 5: high dose ICS plus LABA; For persistent asthma step 6: high dose ICS plus LABA plus oral corticosteroid.

Failure to adequately control symptoms generally indicates a need to progress to the next step. As asthma symptoms worsen, the dosages of the drugs are adjusted. The drugs are beneficial and widely used, but have side effects. In general, dosages of all pharmaceuticals should be limited to the minimum necessary to control the symptoms. Over use of the pharmaceuticals can be a key indicator of a worsening of the asthmatic condition. The regimen is often complicated even before consideration of managing exacerbations and other medical conditions an asthma patient may suffer (co-morbidities). As the population ages, many more in the population suffer from two or more chronic conditions.

Case 1000 can provide information and training for asthmatic patients and their care givers. The case and related systems can address the needs related to managing the treatment of asthma in the following ways:

Before treatment:

Enhance sense of confidence, empowerment and well being, Relief of anxiety regarding readiness to treat the asthma emergency.

Provide immediate, real time assistance in assessing the patient's condition.

Help to remind the patient or care giver to keep the pharmaceuticals close.

Help the patient or care giver locate the pharmaceuticals when needed.

Provide a means for contacting trained professionals for needed information before or during the onset of an asthmatic exacerbation.

Provide information on the expiration and storage of the pharmaceuticals.

Help ensure outdated or recalled pharmaceuticals are disposed of properly and replaced timely.

Provide a history of the interactions related to the patient and the pharmaceuticals prescribed to that patient.

At time of treatment:

Provide emergency voice, visual and data contact with trained professionals to assure proper treatment.

Help ensure that follow-on dosing is given when appropriate and not given when not appropriate.

Help reduce stress.

Record time, location, symptoms, changes in symptoms, adverse reactions, severity of reactions, and progress toward resolution of the asthmatic exacerbation.

Secure professional recommendation for follow on treatment including deciding upon need to transport.

After treatment:

Document treatment and follow up.

Transmit to appropriate electronic medical records.

Ensure expended auto pharmaceutical container is appropriately maintained and eventually disposed of to avoid injury to the patient or others.

Ensure that a replacement pharmaceutical is provided to the patient.

Ensure follow up as recommended is performed.

Ensure added training is offered if required.

Facilitate accumulation of data and analysis to aid in improving the products, services, training, readiness of responders, disease management for the patient and for the asthmatic population.

The following is an example of a use of the case containing a combination of pharmaceuticals in inhalers. In this example, the case contains a Ventolin inhaler which contains albuterol (SABA) and an Advair inhaler which contains salmeterol (LABA) and flucticasone (ICS). These would be the pharmaceutical containers 1021. A tablet of an oral corticosteriod (OCS) is in the secondary medication storage compartment 1018.

Seventeen year old Steve has a history of asthma. Steve is an active young man. He is the kicker for his football team having stopped playing soccer because of exercise induced asthma. Steve uses a SABA inhaler just before exercise. He uses a LABA/ICS inhaler at the onset of symptoms. When he follows these regimes his exacerbations have never been severe. Steve's last severe exacerbation resulted when he forgot to bring his inhaler to a game. During the last severe exacerbation, Steve was in the ambulance before the inhaled medications (borrowed from a fellow student) took effect. Steve's Mom was very concerned and took Steve to his allergist again after the last episode. The allergist advised that these types of reactions could progress and could be life-threatening. He again described the symptoms and effects of asthma, showed Steve and his Mom how and when to use the inhalers. Still, Steve's Mom was concerned. She had also spoken before with the school nurse and the coach were glad that they knew about the benefits of the inhalers. She was concerned when the nurse and the coach described different thoughts about when and how the inhalers should be used. She feared that Steve might be advised to use the pharmaceuticals in an inappropriate way. She was concerned that Steve might not have the pharmaceuticals with him when a threatening asthmatic reaction occurred, that Steve might not recognize the onset of the exacerbation in time to treat himself, might forget exactly how to use the inhalers, etc. When she discussed her concerns, the allergist prescribed case 1000 for Steve. Case 1000 offered could communicate with the same service which monitored patients with life-threatening chronic obstructive airway disease and pulmonary cardiac arrhythmias.

The service set up a protocol with the allergist and trained Steve on the use of case 1000 via the web. Case 1000 was programmed by the service to communicate with Steve's cell phone and automatically communicated with the service when appropriate. For example, when any a pharmaceutical container 1021 (the inhaler) was removed from the case, the communications module 1016 was activated and recorded the removal. Steve was prompted by speaker 1007 to orally or otherwise enter a code via microphone 1008 or otherwise each time the pharmaceutical container 1021 was removed. The communications module could be programmed with voice recognition software and other software. Information regarding these removals and related codes would be stored in the communications module. After a number of removals with a given code or with no code, the communications module communicated with Steve's cell phone. The communications module 1016 in combination with the Steve's 3G GPS equipped cell phone was programmed to contact the service whenever the pharmaceutical container 1021 was removed with a given code or without the entry of a code a certain number of times. The removal of a pharmaceutical container 1021 is sensed by sensor to signal presence or absence of pharmaceutical containers 1021. When a pharmaceutical container 1021 is removed, pharmaceutical container status indicator 1004 associated with one of the two inhalers Steve normally carried in the case changed from green to yellow. Communications module 1016, pharmaceutical container status indicator 1004 and sensors 1030, 1031 and 1038, speaker 1007, microphone 1008, communications module 1016, status indicators 1005, 1006, and camera control 1037 are powered by power source 1025 or by a power source connected to the case through the device connections. Information from the sensors may be stored in the communications module along with the time of the sensor reading. When such events occur Steve's cell phone sent the service information identifying Steve and his location. Under standing instructions, the service would then send reports to Steve's Allergist. Steve's Mom was now far more confident that her son would not be injured or die as a result of misuse, non use or abuse of the pharmaceutical container 1021 (the inhaler).

The service contacted Steve on a schedule agreed upon by his allergist to provide refresher training. The case had been programmed with the expiration date and lot number of the pharmaceutical container 1021 (the inhaler) when it was initially provided. This programming was performed using a barcode reader attached to the device connections 1010. Using this information and an algorithm which calculated depletion of the pharmaceutical in the pharmaceutical container based upon removals from the case, the service provides Steve's allergist and Steve's Mom a reminder to replace the inhaler before the scheduled expiration or the depletion of the pharmaceutical.

Twice in the first month of his use of Case 1000, when Steve forgot to put case 1000 in his backpack, his cell phone called him to remind him to get the inhalers before he even left his house. This was because the communications module 1016 had been programmed to communicate when the case and Steve's cell phone became separated by a distance of more than 20'. As he went back into the house his cell phone was able to poll an RFID chip on the case to help Steve locate the case. Had he not been able to locate the case and remain within the specified distance; after a programmed time interval, the service and Steve's Mom would have been contacted.

About six months after Steve first received case 1000, he went on a road game with his football team. The game was in January in a city with a high elevation. Just after the kickoff, Steve when back to the bench and experienced a severe, sudden-onset asthma exacerbation.

Steve located case 1000 case in his overstuffed backpack by tactile sense. Steve opened the case and removed the inhaler. Because of the severity Steve voiced the words "panic attack" into the microphone 1008 on case 1000. Very quickly, his cell phone rang with a special ring tone indicating that the service was calling. By this time Steve had already successfully used his inhaler (the pharmaceutical container 1021). He was a little shaken, but answered the call. He passed the phone to the coach. She spoke with the service and sent a FEV1 reading, a stethoscopic recording of Steve's breathing and a photo of Steve to the service using his cell phone. The service called Steve's his allergist's emergency call line. It seemed that Steve was OK. The service advised the coach how to monitor Steve's condition while a video consultation with the allergist could be arranged. The consultation revealed that Steve had forgotten to take his daily OCS. He removed the secondary medication 19 (the OCS) from the secondary medication storage compartment 1018 and took the OCS.

Steve placed the used pharmaceutical container 1027 (the activated inhaler) back into the case. When he did so, case 1000 recorded that this inhaler had been associated with this event. A notice was sent to Steve's allergist.

Within a short time, Steve's symptoms had disappeared. The allergist decided that transport to the emergency room was not required. When the bus returned to Steve's hometown, Steve's Mom picked him up and drove Steve for an exam at the allergist's office. The exam confirmed that no further treatment was required. The allergist used the events to reinforce the training and directed that case 1000 be programmed to provide more frequent compliance reminders. Even though the inhaler which Steve had used still contained a few doses, the allergist suggested that he retain the inhalers.

Had the allergist suspected that the inhalers might have been defective or had there been an adverse reaction, the allergist could have taken further steps to report any defect or adverse reaction.

On the way home, Steve and his Mom stopped by their pharmacy to pick up a new inhaler and have case 1000 case reprogrammed. The service sent a report to the allergist which the allergist's practice management software placed in Steve's electronic medical record. A copy of this updated record was also sent to Steve's primary care physician.

The numbers of asthma-related hospital admissions and deaths shows that better management could yield important savings and decreased mortality. Inadequate management such as is the case today may result in the unnecessary deaths, dispatch of an ambulance and transport, emergency department visits, hospital admissions, intubations, events associated with hospitalization (medication errors and nosocomial infections), and insurance claims for all these events. In this example using case 1000 system avoided the potential for ambulance for all these costs. The costs of these events depend upon the specifics of the situation including geographic location. The costs may reach thousands of dollars per event. Avoiding these costs, other indirect costs and the stresses associated with emergency room visits is beneficial to the patient, caregivers, and society.

Although illustrative embodiments of the present invention, and various modifications thereof, have been described in detail herein with reference to the accompanying drawings, it is to be understood that the invention is not limited to these precise embodiments and the described modifications, and that various changes and further modifications may be effected therein by one skilled in the art without departing from the scope or spirit of the invention as defined in the appended claims.

What is claimed is:

1. A container for a product, comprising:
   a location circuit for determining the location of the container,
   a storage element for storing an access code for a central facility, and a container identification code,
   a plurality of data acquisition components for acquiring status of at least two characteristics of at least one of the container, the product and a user of the product, one of the characteristics indicating use of the product, and
   a communication interface for generating and sending an event communication signal including
   (a) the access code for the central facility,
   (b) the container identification code from the storage element,
   (c) the location of the container from the location circuit, and
   (d) the status of the at least two characteristics from the data acquisition components.

2. The container of claim 1, wherein the container is an auto-injector for containing a medicament.

3. The container of claim 1, wherein the container is a case.

4. The container of claim 1, wherein the location circuit uses the global positioning system (GPS).

5. The container of claim 1, wherein one of the data acquisition components is a camera.

6. The container of claim 1, wherein the data acquisition components include at least one sensor for sensing at least one of a thermal image, vibration, temperature, humidity, a chemical and an audio signal.

7. The container of claim 1, wherein one of the data acquisition components is for sensing multiple events.

8. The container of claim 7, wherein the data acquisition component for sensing multiple events is a sound sensor.

9. A container for a product, comprising:
   a location circuit for determining the location of the container,
   a storage element for storing an access code for a central facility, and a container identification code,
   a plurality of data acquisition components for acquiring status of at least two characteristics of at least one of the container, the product and a user of the product, at least one of the characteristics indicating lack of use of at least one of the container and the product, and
   a communication interface for generating and sending an event communication signal including
   (a) the access code for the central facility,
   (b) the container identification code from the storage element,
   (c) the location of the container from the location circuit, and
   (d) the status of the at least two characteristics from the data acquisition components.

10. The container of claim 1 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

11. A container for a product, the container for use with an external device having long-range communication capability and short-range communication capability and location sensing capability, comprising:
    a status indicator for indicating whether the product has been used,
    a storage element for storing an access code for a central facility and a container identification code,
    a plurality of data acquisition components for acquiring status of at least two characteristics of at least one of the container, the product and a user of the product,
    a local communication interface for communicating with the external device using the short-range communication capability of the external device, and
    a processor for producing information and directing the local communication interface to send the information to the external device, the information including:
    (a) the access code for the central facility,
    (b) the container identification code,
    (c) the status of at least two characteristics from the data acquisition components,
    (d) instructions for the external device to use its location sensing capability to sense its location and to report its sensed location to the central facility along with (b) and (c), using its long-range communication capability and (a).

12. The container of claim 11, wherein the container is an auto-injector for containing a medicament.

13. The container of claim 11, wherein the container is a case.

14. A container for a product, the container for use with an external device having a camera, long-range communication capability and short-range communication capability and location sensing capability, comprising:
    a storage element for storing an access code for a central facility and a container identification code,
    a plurality of data acquisition components for acquiring status of at least two characteristics of at least one of the container, the product and a user of the product, a local communication interface for communicating with the external device using the short-range communication capability of the external device, and for producing an instruction to a user of the external device to use the camera to capture at least one image, for producing information, and for directing the local communication interface to send the information to the external device, the information including:
(a) the access code for the central facility,
(b) the container identification code,
(c) the status of at least two characteristics from the data acquisition components,
(d) instructions for the external device to use its location sensing capability to sense its location and to report its sensed location to the central facility along with (b) and (c) and the at least one captured image to the central facility, using its long-range communication capability and (a).

15. The container of claim 14, wherein the at least one captured image is a video sequence.

16. The container of claim 11, wherein the data acquisition components include at least one sensor for sensing at least one of a thermal image, vibration, temperature, humidity and an audio signal.

17. The container of claim 11, wherein the external device is a handheld portable communications device.

18. The container of claim 11, wherein the external device is a practice management system for at least one of dentistry and medicine.

19. The container of claim 11, further comprising a speaker, and wherein the local communication interface is also for receiving a poll signal from the external device and the processor is also for instructing the speaker to generate an audible noise in response to the poll signal.

20. The container of claim 11, further comprising a primary compartment for storing a first medication, and a second compartment for storing a second medication.

21. A container for a product, the container for use with an external device having long-range communication capability and short-range communication capability and location sensing capability, comprising:
a storage element for storing an access code for a central facility and a container identification code,
a plurality of data acquisition components for acquiring status of at least two characteristics of at least one of the container, the product and a user of the product,
a local communication interface for communicating with the external device using the short-range communication capability of the external device, and
a processor for producing information and directing the local communication interface to send the information to the external device, the information including:
(a) the access code for the central facility,
(b) the container identification code,
(c) the status of at least two characteristics from the data acquisition components,
(d) instructions for the external device to use its location sensing capability to sense its location and to report its sensed location to the central facility along with (b) and (c), using its long-range communication capability and (a),
wherein the processor is also for directing the local communication device to send a signal to the external device to activate its long-range communication capability, the signal indicating that a user of the container requests communication.

22. A container for a product, the container for use with an external device having long-range communication capability and short-range communication capability and location sensing capability, comprising:
a storage element for storing an access code for a central facility and a container identification code,
a plurality of data acquisition components for acquiring status of at least two characteristics of at least one of the container, the product and a user of the product,
a local communication interface for communicating with the external device using the short-range communication capability of the external device, and
a processor for producing information and directing the local communication interface to send the information to the external device, the information including:
(a) the access code for the central facility,
(b) the container identification code,
(c) the status of at least two characteristics from the data acquisition components,
(d) instructions for the external device to use its location sensing capability to sense its location and to report its sensed location to the central facility along with (b) and (c), using its long-range communication capability and (a),
wherein the processor is also for directing the local communication device to send a signal to the external device to activate its long-range communication capability, the signal indicating that the product has been removed from the container a predetermined number of times.

23. A container for a product, the container for use with an external device having long-range communication capability and short-range communication capability and location sensing capability, comprising:
a storage element for storing an access code for a central facility and a container identification code,
a plurality of data acquisition components for acquiring status of at least two characteristics of at least one of the container, the product and a user of the product,
a local communication interface for communicating with the external device using the short-range communication capability of the external device, and
a processor for producing information and directing the local communication interface to send the information to the external device, the information including:
(a) the access code for the central facility,
(b) the container identification code,
(c) the status of at least two characteristics from the data acquisition components,
(d) instructions for the external device to use its location sensing capability to sense its location and to report its sensed location to the central facility along with (b) and (c), using its long-range communication capability and (a), and
a control switch,
wherein the processor is also for directing the local communication device to send a signal to the external device to activate its long-range communication capability, the signal indicating that the control switch has been activated.

24. The container of claim 11, further comprising a sensor, and wherein the processor is also for directing the local communication interface to send a signal to the external device to activate its long-range communication capability, the signal indicating that the sensor has sensed a specified condition.

25. A container for a product, comprising:
a status indicator for indicating whether the product has been used, a location circuit for determining the location of the container, a storage element for storing an access code for a central facility, and a container identification code, a plurality of data acquisition components for acquiring status of at least two characteristics of at least one of the container, the product and a user of the product, and a communication interface for generating and sending an event communication signal including (a) the access code for the central facility, (b) the container identification code from the storage element, (c) the location of the container from the location circuit, and (d) the status of the at least two characteristics from the data acquisition components.

26. The container of claim 1, further comprising a primary compartment for storing a first medication, and a second compartment for storing a second medication.

27. A container for a product, comprising:

a location circuit for determining the location of the container, a storage element for storing an access code for a central facility, and a container identification code, a plurality of data acquisition components for acquiring status of at least two characteristics of at least one of the container, the product and a user of the product, and a communication interface for generating and sending an event communication signal including (a) the access code for the central facility, (b) the container identification code from the storage element, (c) the location of the container from the location circuit, and (d) the status of the at least two characteristics from the data acquisition components, wherein the communication interface is also for generating and sending an exception signal indicating that a user of the container requests communication.

28. A container for a product, comprising:

a location circuit for determining the location of the container, a storage element for storing an access code for a central facility, and a container identification code, a plurality of data acquisition components for acquiring status of at least two characteristics of at least one of the container, the product and a user of the product, and a communication interface for generating and sending an event communication signal including (a) the access code for the central facility, (b) the container identification code from the storage element, (c) the location of the container from the location circuit, and (d) the status of the at least two characteristics from the data acquisition components, wherein the communication interface is also for generating and sending an exception signal indicating that the product has been removed from the container a predetermined number of times.

29. A container for a product, comprising:

a control switch, a location circuit for determining the location of the container, a storage element for storing an access code for a central facility, and a container identification code, a plurality of data acquisition components for acquiring status of at least two characteristics of at least one of the container, the product and a user of the product, and a communication interface for generating and sending an event communication signal including (a) the access code for the central facility, (b) the container identification code from the storage element, (c) the location of the container from the location circuit, and (d) the status of the at least two characteristics from the data acquisition components, wherein the communication interface is also for generating and sending an exception signal indicating that the control switch has been activated.

30. The container of claim 1, wherein the container is an inhaler for containing a medicament.

31. The container of claim 11, wherein the container is an inhaler for containing a medicament.

32. The container of claim 1, wherein the container is for containing a medicament.

33. The container of claim 9, wherein the container is for containing a medicament.

34. The container of claim 25, wherein the container is for containing a medicament.

35. The container of claim 27, wherein the container is for containing a medicament.

36. The container of claim 28, wherein the container is for containing a medicament.

37. The container of claim 29, wherein the container is for containing a medicament.

38. The container of claim 11, wherein the container is for containing a medicament.

39. The container of claim 14, wherein the container is for containing a medicament.

40. The container of claim 21, wherein the container is for containing a medicament.

41. The container of claim 22, wherein the container is for containing a medicament.

42. The container of claim 23, wherein the container is for containing a medicament.

43. The container of claim 9, wherein the container is a case.

44. The container of claim 25, wherein the container is a case.

45. The container of claim 27, wherein the container is a case.

46. The container of claim 28, wherein the container is a case.

47. The container of claim 29, wherein the container is a case.

48. The container of claim 14, wherein the container is a case.

49. The container of claim 21, wherein the container is a case.

50. The container of claim 22, wherein the container is a case.

51. The container of claim 23, wherein the container is a case.

52. The container of claim 3, wherein the case is for containing at least two medicament holding devices.

53. The container of claim 13, wherein the case is for containing at least two medicament holding devices.

54. The container of claim 1, wherein the location circuit senses proximity to an external communication device.

55. The container of claim 9, wherein the location circuit senses proximity to an external communication device.

56. The container of claim 25, wherein the location circuit senses proximity to an external communication device.

57. The container of claim 27, wherein the location circuit senses proximity to an external communication device.

58. The container of claim 28, wherein the location circuit senses proximity to an external communication device.

59. The container of claim 29, wherein the location circuit senses proximity to an external communication device.

60. The container of claim 11, wherein the external device also has a device local location circuit, and further comprising a container local location circuit for sensing proximity to the device local location circuit.

61. The container of claim 14, wherein the external device also has a device local location circuit, and further comprising a container local location circuit for sensing proximity to the device local location circuit.

62. The container of claim 21, wherein the external device also has a device local location circuit, and further comprising a container local location circuit for sensing proximity to the device local location circuit.

63. The container of claim 22, wherein the external device also has a device local location circuit, and further comprising a container local location circuit for sensing proximity to the device local location circuit.

64. The container of claim 23, wherein the external device also has a device local location circuit, and further comprising a container local location circuit for sensing proximity to the device local location circuit.

65. The container of claim 1, wherein use of the product is when the container is being carried by a person.

66. The container of claim 25, wherein use of the product is when the container is being carried by a person.

67. The container of claim 11, wherein use of the product is when the container is being carried by a person.

68. The container of claim 1, wherein the product is a medicament, and use of the product is when the medicament is being released from the container.

69. The container of claim 25, wherein the product is a medicament, and use of the product is when the medicament is being released from the container.

70. The container of claim 11, wherein the product is a medicament, and use of the product is when the medicament is being released from the container.

71. The container of claim 9 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

72. The container of claim 25 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

73. The container of claim 27 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

74. The container of claim 28 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

75. The container of claim 29 for use with an external device having long-range communication capability and short-range communication capability, wherein the communication interface sends the event signal to the external device via a short-range communication channel, and the external device contacts the central facility using the access code and provides elements (b)-(d) of the event signal to the central facility.

76. The container of claim 10, wherein the external device is a cellphone.

77. The container of claim 71, wherein the external device is a cellphone.

78. The container of claim 72, wherein the external device is a cellphone.

79. The container of claim 73, wherein the external device is a cellphone.

80. The container of claim 74, wherein the external device is a cellphone.

81. The container of claim 75, wherein the external device is a cellphone.

82. The container of claim 11, wherein the external device is a cellphone.

83. The container of claim 10, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

84. The container of claim 71, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

85. The container of claim 72, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

86. The container of claim 73, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

87. The container of claim 74, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

88. The container of claim 75, wherein the external device has a relative location circuit for cooperating with the location circuit in the container, and has an absolute location circuit for determining its own geographic location, and wherein when the external device provides elements (b)-(d) of the event signal to the central facility, the external devices also provides its own geographic location to the central facility.

89. The container of claim 14, wherein the external device is a handheld portable communications device.

90. The container of claim 21, wherein the external device is a handheld portable communications device.

91. The container of claim 22, wherein the external device is a handheld portable communications device.

92. The container of claim 23, wherein the external device is a handheld portable communications device.

93. The container of claim 14, wherein the external device is a practice management system for at least one of dentistry and medicine.

94. The container of claim 21, wherein the external device is a practice management system for at least one of dentistry and medicine.

95. The container of claim 22, wherein the external device is a practice management system for at least one of dentistry and medicine.

96. The container of claim 23, wherein the external device is a practice management system for at least one of dentistry and medicine.

* * * * *

UNITED STATES PATENT AND TRADEMARK OFFICE
CERTIFICATE OF CORRECTION

PATENT NO. : 8,044,778 B2 Page 1 of 1
APPLICATION NO. : 12/319792
DATED : October 25, 2011
INVENTOR(S) : O. Napoleon Monroe It is certified that error appears in the above-identified patent and that said Letters Patent is hereby corrected as shown below:

Col. 44, Claim 14, line 13, before "for producing an instruction to a user of the external device", insert -- a processor --.

Col. 45, Claim 16, line 1, change "claim 11" to -- claim 14 --.

Col. 45, Claim 17, line 1, change "claim 11" to -- claim 14 --.

Col. 45, Claim 18, line 1, change "claim 11" to -- claim 14 --.

Col. 45, Claim 19, line 1, change "claim 11" to -- claim 14 --.

Col. 45, Claim 20, line 1, change "claim 11" to -- claim 14 --.

Signed and Sealed this
Twenty-third Day of October, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO.        : 8,044,778 B2
APPLICATION NO.   : 12/319792
DATED             : October 25, 2011
INVENTOR(S)       : O. Napoleon Monroe It is certified that error appears in the above-identified patent and that said Letters Patent is hereby corrected as shown below:

Column 45, line 4 (Claim 14, line 13) before "for producing an instruction to a user of the external device", insert -- a processor --.

Column 45, line 22 (Claim 16, line 1) change "claim 11" to -- claim 14 --.

Column 45, line 26 (Claim 17, line 1) change "claim 11" to -- claim 14 --.

Column 45, line 28 (Claim 18, line 1) change "claim 11" to -- claim 14 --.

Column 45, line 31 (Claim 19, line 1) change "claim 11" to -- claim 14 --.

Column 45, line 36 (Claim 20, line 1) change "claim 11" to -- claim 14 --.

This certificate supersedes the Certificate of Correction issued October 23, 2002.

Signed and Sealed this
Thirteenth Day of November, 2012

David J. Kappos
*Director of the United States Patent and Trademark Office*